United States Patent
Leeper et al.

(10) Patent No.: US 10,329,354 B2
(45) Date of Patent: Jun. 25, 2019

(54) MODULATION OF EFFEROCYTOSIS PATHWAYS FOR TREATMENT OF ATHEROSCLEROTIC DISEASE

(71) Applicant: The Board of Trustees of the Leland Stanford Junior University, Stanford, CA (US)

(72) Inventors: Nicholas J. Leeper, Stanford, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/916,517

(22) PCT Filed: Sep. 15, 2014

(86) PCT No.: PCT/US2014/055680
§ 371 (c)(1),
(2) Date: Mar. 3, 2016

(87) PCT Pub. No.: WO2015/041987
PCT Pub. Date: Mar. 26, 2015

(65) Prior Publication Data
US 2016/0194406 A1    Jul. 7, 2016

Related U.S. Application Data

(60) Provisional application No. 61/879,562, filed on Sep. 18, 2013.

(51) Int. Cl.
| | | |
|---|---|---|
| *A61K 38/17* | (2006.01) | |
| *A61K 39/00* | (2006.01) | |
| *C07K 16/28* | (2006.01) | |
| *C07K 16/40* | (2006.01) | |
| *C12Q 1/6883* | (2018.01) | |
| *A61K 31/519* | (2006.01) | |
| *A61K 31/7068* | (2006.01) | |

(52) U.S. Cl.
CPC ............ *C07K 16/40* (2013.01); *A61K 31/519* (2013.01); *A61K 31/7068* (2013.01); *A61K 38/177* (2013.01); *A61K 38/1738* (2013.01); *A61K 38/1774* (2013.01); *C07K 16/2803* (2013.01); *C12Q 1/6883* (2013.01); *A61K 2039/505* (2013.01); *C07K 2317/24* (2013.01); *C07K 2317/31* (2013.01); *C07K 2317/76* (2013.01); *C12Q 2600/106* (2013.01); *C12Q 2600/156* (2013.01)

(58) Field of Classification Search
CPC ............ A61K 38/177; A61K 38/1774; A61K 38/1738; A61K 2039/505; C07K 16/40; C07K 16/2803; C07K 2317/31; C07K 2317/76; C12Q 1/6883; C12Q 2600/106; C12Q 2600/156
See application file for complete search history.

(56) References Cited

U.S. PATENT DOCUMENTS

| | | | |
|---|---|---|---|
| 8,492,096 B2 | 7/2013 | Pasche | |
| 2001/0021380 A1 | 9/2001 | Pluenneke et al. | |
| 2008/0267909 A1 | 10/2008 | Tabas | |
| 2010/0092467 A1* | 4/2010 | Isenberg | C07K 14/78 424/133.1 |
| 2012/0039896 A1 | 2/2012 | Clemmons et al. | |
| 2012/0269731 A1 | 10/2012 | Wellstein et al. | |
| 2014/0161799 A1 | 6/2014 | Frazier et al. | |

FOREIGN PATENT DOCUMENTS

| | | | |
|---|---|---|---|
| WO | WO1996036643 A1 | 11/1996 | |
| WO | 1999/040940 A1 | 8/1999 | |
| WO | 00/18232 A1 | 4/2000 | |
| WO | 00/20577 A1 | 4/2000 | |
| WO | 2001/035986 A2 | 5/2001 | |
| WO | 2001/043743 A1 | 6/2001 | |
| WO | 2006/034154 A2 | 3/2006 | |
| WO | 2010/070047 A1 | 6/2010 | |
| WO | 2010/083253 A2 | 7/2010 | |
| WO | WO2011/143624 | * 11/2011 | |
| WO | 2012/170250 A1 | 12/2012 | |
| WO | 2013/032883 A2 | 3/2013 | |
| WO | WO2013109752 A1 | 7/2013 | |

(Continued)

OTHER PUBLICATIONS

Moore et al. 'The Cellular Biology of Macrophages in Atherosclerosis,' Cell, 29 Apr. 29, 2011, pp. 341-355, vol. 45, Elsevier Inc., New York USA.

Holdt et al., "Expression of Chr9p21 genes CDKN2B (p15(1NK4b)), CDKN2A (p16(1NK4a), p14(ARF)) and MTAP in human atherosclerotic plaque", Atherosclerosis, Jun. 15, 2010, pp. 264-270, 214, Elsevier, Amsterdam, NL.

Dai et al., "Calreticulin, a Potential Vascular Regulatory Protein, Reduces Intimal Hyperplasia After Arterial Injury" Arteriosclerosis, Thrombosis, and Vascular Biology, Nov. 1, 1997, pp. 2359-2368, vol. 17, Issue 11, American Heart Association, Inc., Dallas, TX.

Narizhneva et al., "Thrombospondin-1 up-regulates expression of cell adhesion molecules and promotes monocyte binding to endothelium" The FASEB Journal, Apr. 15, 2005, pp. 1158-1160, vol. 19 No. 9, FASEB, Cleveland, OH.

(Continued)

*Primary Examiner* — Robert S Landsman
*Assistant Examiner* — Bruce D. Hissong
(74) *Attorney, Agent, or Firm* — Pamela J. Sherwood; Bozicevic, Field & Francis LLP

(57) ABSTRACT

Smooth muscle cells (SMC) from subjects carrying at least one 9p21 risk factor, can be resistant to efferocytosis, leading to the retention of such cells in the necrotic core of atherosclerotic plaque. In the methods of the invention, an agent that increases efferocytosis of cellular components of coronary plaque, including efferocytosis of apoptotic smooth muscle cells, is administered to the subject in a dose and for a period of time effective to stabilize, prevent or reduce atherosclerotic plaque in the individual.

9 Claims, 16 Drawing Sheets

Specification includes a Sequence Listing.

(56) References Cited

FOREIGN PATENT DOCUMENTS

| WO | 2014/124028 A1 | 8/2014 |
| WO | 2014/149477 A1 | 9/2014 |
| WO | 2015/041987 A1 | 3/2015 |
| WO | 2016/044021 A1 | 3/2016 |

OTHER PUBLICATIONS

Isenberg et al., "Blocking Thrombospondin-1/CD47 Signaling Alleviates Deleterious Effects of Aging on Tissue Responses to Ischemia" Arteriosclerosis, Thrombosis, and Vascular Biology, Nov. 20, 2007, pp. 2582-2588, vol. 27, Issue 12, American Heart Association, Dallas, TX.

Kojima et al., "CD47-blocking antibodies restore phagocytosis and prevent atherosclerosis", Nature, Jul. 28, 2016, pp. 86-98, vol. 536, No. 7614, Springer Nature, Basingstoke, United Kingdom.

Faruqi, "Reactivating cellular rubbish removal ameliorates atherosclerosis: Cardiovascular disease", Nature Reviews Drug Discovery, Aug. 19, 2016, p. 682, vol. 15, No. 9, Macmillan Publishers Limited, London, United Kingdom.

\* cited by examiner

MODULATION OF EFFEROCYTOSIS PATHWAYS FOR TREATMENT OF ATHEROSCLEROTIC DISEASE

GOVERNMENT SUPPORT

The following invention was made with Government support under contract HL103605 by the National Institutes of Health. The Government has certain rights in the invention.

BACKGROUND OF THE INVENTION

Atherosclerotic cardiovascular disease (ASCVD) remains the primary cause of morbidity and mortality worldwide. Patients with ASCVD represent a heterogeneous group of individuals, with a disease that progresses at different rates and in distinctly different patterns. Despite appropriate evidence-based treatments for patients with ASCVD, recurrence and mortality rates remain 2-4% per year.

In general, atherosclerosis is believed to be a complex disease involving multiple biological pathways. Variations in the natural history of the atherosclerotic disease process, as well as differential response to risk factors and variations in the individual response to therapy, reflect in part differences in genetic background and their intricate interactions with the environmental factors that are responsible for the initiation and modification of the disease. Atherosclerotic disease is also influenced by the complex nature of the cardiovascular system itself where anatomy, function and biology all play important roles in health as well as disease.

Traditional risk factors account for approximately half of an individual's lifetime risk of cardiovascular disease. The balance, therefore, is accounted for by a combination of unmeasured environmental exposures and genetic factors. The recent advent of the genome-wide association study (GWAS) platform has made it possible to investigate the heritable component of complex polygenic disorders, such as atherosclerotic coronary artery disease (CAD). Using this approach, a region on chromosome 9p21.3 has repeatedly been identified in GWAS as the top locus for complex cardiovascular disease (Helgadottir et al. (2007) *Science* 316:1491-1493; McPherson et al. (2007) *Science* 316:1488-1491).

Available data suggest that the risk-associated polymorphisms: 1) are very common, with as much as a fifth of the world population carrying two copies of the risk allele (minor allele frequency ~50%) (Deloukas et al. (2013) Nat Genet 45:25-33); 2) are independent of all established risk factors, suggesting a novel mechanism of action (Cunnington and Keavney (2011) Curr Atheroscler Rep 13:193-201); 3) are responsible for up to 21% of the attributable risk of myocardial infarction (MI); and 4) promote risk across a spectrum of vascular diseases, including CAD, stroke, peripheral artery disease (PAD) and abdominal aortic aneurysm (AAA) (Helgadottir et al. (2008) *Nat Genet* 40:217-224).

Elucidating the vascular biology of the 9p21 locus has become a priority for the scientific community. Because the most highly associated single nucleotide polymorphisms (SNPs) occur in a noncoding region of the genome, a number of expression quantitative trait locus (eQTL) and allelic expression imbalance (AEI) studies have been performed in an attempt to identify the causal gene(s) which are dysregulated in carriers of the 9p21 risk variant. Though a variety of associations have been reported, reduced expression of the nearby tumor-suppressor gene, CDKN2B, has now been observed in several tissues from carriers of the risk allele, including adipose tissue and circulating cells (Liu et al. (2009) *PLoS ONE* 4:e5027; Schunkert et al. (2011) *Nat Genet* 43:333-338), as well as in the 'end organ', including atherosclerotic plaque and vascular smooth muscle cells (SMCs), (Pilbrow et al. 2012. *PLoS One* 7:e39574).

Atherosclerotic plaque consists of accumulated intracellular and extracellular lipids, smooth muscle cells, connective tissue, and glycosaminoglycans. The earliest detectable lesion of atherosclerosis is the fatty streak, consisting of lipid-laden foam cells, which are macrophages that have migrated as monocytes from the circulation into the subendothelial layer of the intima, which later evolves into the fibrous plaque, consisting of intimal smooth muscle cells surrounded by connective tissue and intracellular and extracellular lipids.

SUMMARY OF THE INVENTION

Methods are provided for the prevention and treatment of coronary artery disease (CAD) in a subject, including without limitation methods of preventing or treating atherosclerosis. In some embodiments, the subject is homozygous or heterozygous for a 9p21 risk allele. In some such embodiments the methods include genetic testing of the subject for the presence of a 9p21 risk allele. In other such embodiments the subject has been previously diagnosed for the presence of a 9p21 risk allele, where such methods may include, without limitation, analyzing a sample of genomic DNA from the individual for the presence of sequences of human chromosome 9p21 associated risk of CAD, including SNPs associated with the risk locus.

The methods of the invention are based in part on the finding that apoptotic smooth muscle cells (SMC) in carriers of the risk allele can be resistant to efferocytosis, leading to the retention of such cells in the necrotic core of atherosclerotic plaque. In the methods of the invention, an agent that increases efferocytosis of cellular components of coronary plaque, including efferocytosis of apoptotic smooth muscle cells, is administered to the subject in a dose and for a period of time effective to stabilize, prevent or reduce atherosclerotic plaque in the individual.

Molecular targets for increasing efferocytosis include, without limitation, agents that activate or increase expression of CDKN2B or Retinoblastoma (Rb), or decrease the expression of E2F4; agents that increase activity or expression of calreticulin; agents that block the interaction of CD47 and SIRPα; and the like.

Another aspect of the present invention relates to the use of an efferocytosis stimulating agent in the manufacture of a medicament to stabilize, prevent or reduce atherosclerotic plaque, wherein the medicament is administered to an individual having or at risk of having atherosclerosis.

Still another aspect of the present invention provides a kit to stabilize, prevent or reduce atherosclerotic plaque. The kit includes an efferocytosis stimulating agent, in an amount sufficient to stabilize, prevent or reduce atherosclerotic plaque. The kit may also include reagents for genotyping at human chromosome 9p21, including alleles of rs10757278 and rs1333049. The kit may also instructions for use, reagents for monitoring atherosclerotic disease, and the like.

In other embodiments the agent enhances expression of CDKN2B in cardiovascular cells, including, for example, smooth muscle cells. Such agents may include, for example, palbociclib; 5-aza-2'-deoxycytidine in the absence or presence of phenylbutyrate; etc.

In some embodiments, the agent that increases efferocytosis reduces the interaction of CD47 and SIRPα, which agent may be referred to herein as an anti-CD47 agent. In some embodiments such agents do not interfere with the interaction between CD47 and thrombospondin. Preferred anti-CD47 agents include soluble SIRPα, for example a high affinity soluble SIRPα; anti-CD47 antibodies, anti-SIRPα antibodies, etc.

In some embodiments the agent mimics or enhances calreticulin. Calreticulin "mimetics" and "agonists" include molecules that function similarly to, or potentiate, CRT by binding and activating LRP receptor. Molecules useful as CRT mimetics include derivatives, variants, and biologically active fragments of naturally occurring CRT. Molecules useful as agonists include antibodies and other agents that act to enhance the pro-phagocytic activity of CRT.

In other embodiments, methods are provided for screening candidate agents for treatment of CAD, including without limitation CAD associated with 9p21 risk allele(s), by determining the effect of an agent on a target in the efferocytosis pathway, e.g. CDKN2B, calreticulin, CD47, etc.

Figure 6:
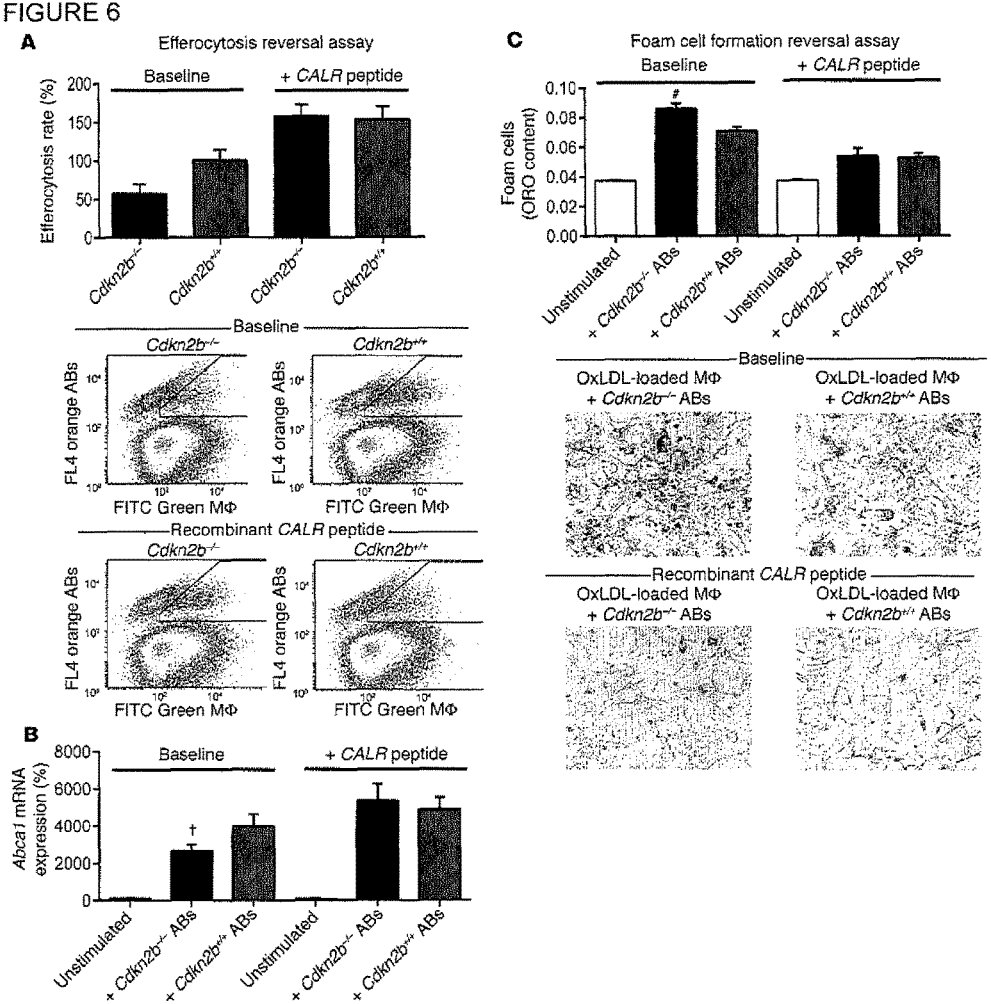

FIG. 6. The Cdkn2b-dependent defect in efferocytosis is reversible. (A) Application of exogenous CALR peptide abrogates the baseline difference in engulfment rates observed between Cdkn2b$^{-/-}$ ABs and Cdkn2b$^{+/+}$ ABs. Exogenous CALR peptide also normalizes the baseline differences in Abca1 expression (B) and foam cell formation (C). Original magnification, 20×. P<0.01; $_+$P<0.03.

Figure 1:
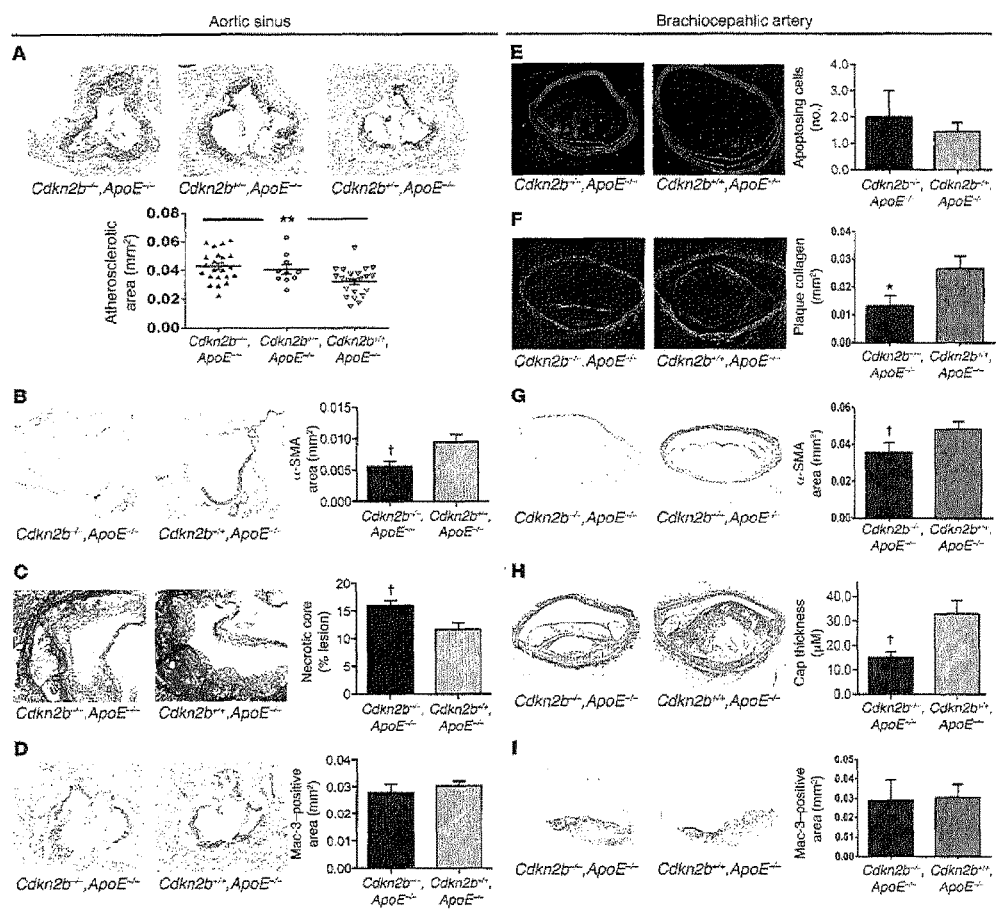
FIG. 1. Cdkn2b regulates atherosclerotic lesion size and growth of the necrotic core. (A) Compared to Cdkn2b$^{+/+}$, ApoE$^{-/-}$ control mice (n=22), Cdkn2b$^{-/-}$,ApoE$^{-/-}$ (n=22) mice developed significantly larger aortic sinus atherosclerotic plaques, as assessed by Oil Red O positive area. (B) These lesions displayed reduced SMC α-actin content and (C) larger necrotic cores, with (D) no increase in macrophage burden. (E) Only a trend towards a higher rate of apoptosis could be detected in Cdkn2b$^{-/-}$,ApoE$^{-/-}$ animals at the terminal timepoint. (F) The brachiocephalic artery lesions in Cdkn2b$^{-/-}$,ApoE$^{-/-}$ mice displayed several features of lesion vulnerability, including reduced plaque collagen content, (G) reduced SMC content and cap coverage, and (H) thinning of the fibrous cap overlying the necrotic core. (I) No difference in macrophage burden was appreciated in the brachiocephalic lesions across genotypes. *=P<0.05; +=P<0.03; #=P<0.01; **=P<0.001.
Figure 7:
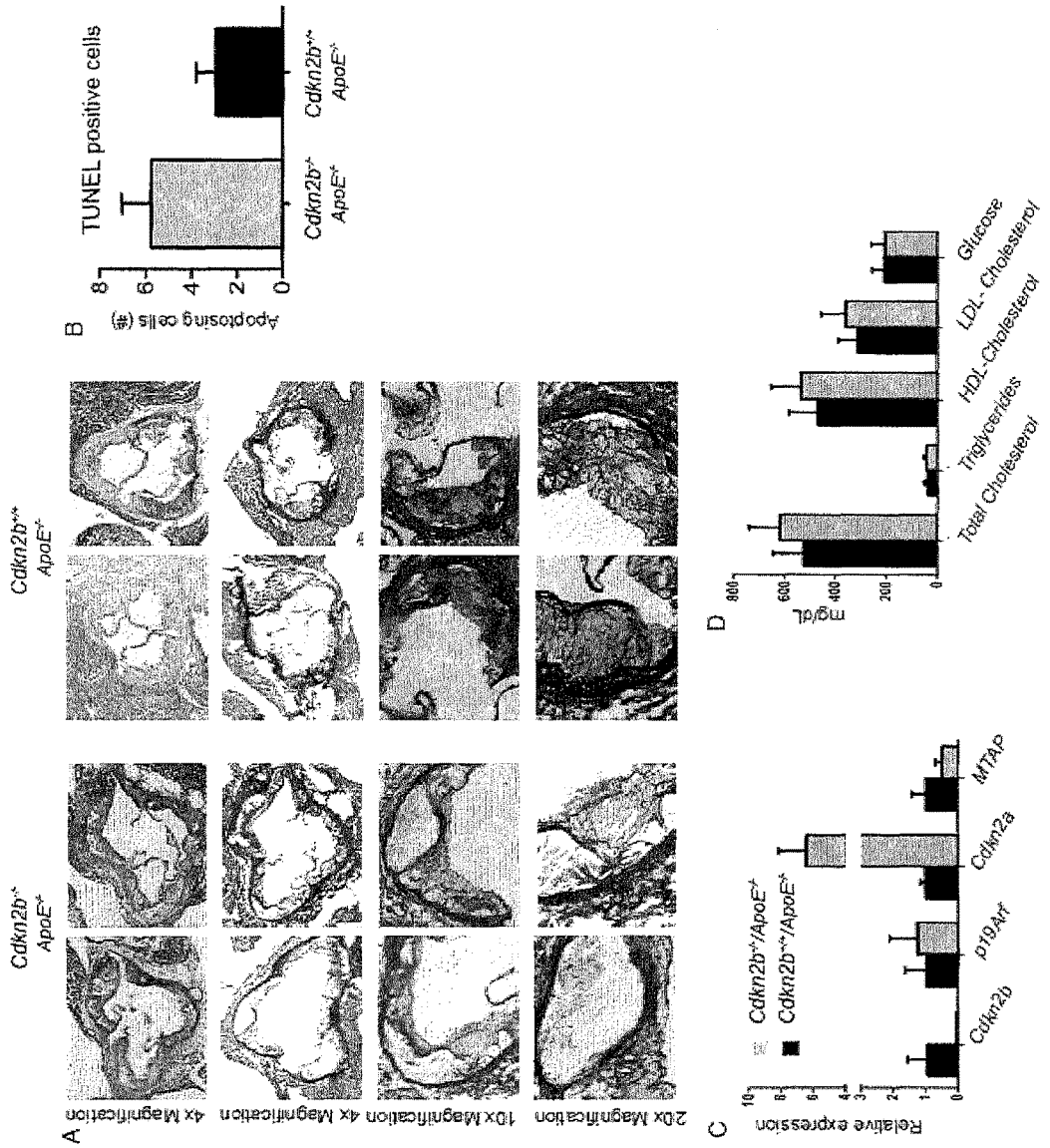

FIG. 7. Loss of Cdkn2b increases growth of the necrotic core and increases early apoptosis. (A) Additional examples of the large acellular necrotic cores observed in Cdkn2b$^{-/-}$ ApoE$^{-/-}$ mice relative to Cdkn2b$^{+/+}$,ApoE$^{-/-}$ control animals (H&E staining on top, Masson Trichrome on bottom at various magnifications). (B) Because very little apoptosis was observed at the terminal endpoint of the chronic model provided in FIG. 1, an additional 10 Cdkn2b$^{+/+}$,ApoE$^{-/-}$ and Cdkn2b$^{-/-}$,ApoE$^{-/-}$ who had only received four weeks of high-fat diet were infused with Angiotensin II by osmotic minipump for 72 hours prior to sacrifice to induce acute vascular inflammation. In this case, Cdkn2b$^{-/-}$,ApoE$^{-/-}$ displayed a 97% increase in TUNEL positive cells per section relative to controls, of borderline significance (P=0.06). (C) Compensation of other 9p21.3 locus genes in aortic tissue from Cdkn2b$^{-/-}$,ApoE$^{-/-}$ relative to Cdkn2b$^{+/+}$, ApoE$^{-/-}$ control mice. As previously described, there is significant upregulation of Cdkn2a in Cdkn2b knockout animals. In the current studies, no difference in the expression of the pro-apoptotic gene p19/Arf was observed at the terminal endpoint. (D) No difference in lipid levels or fasting glucose was observed between genotypes after 12 weeks of Western diet.

Figure 8:
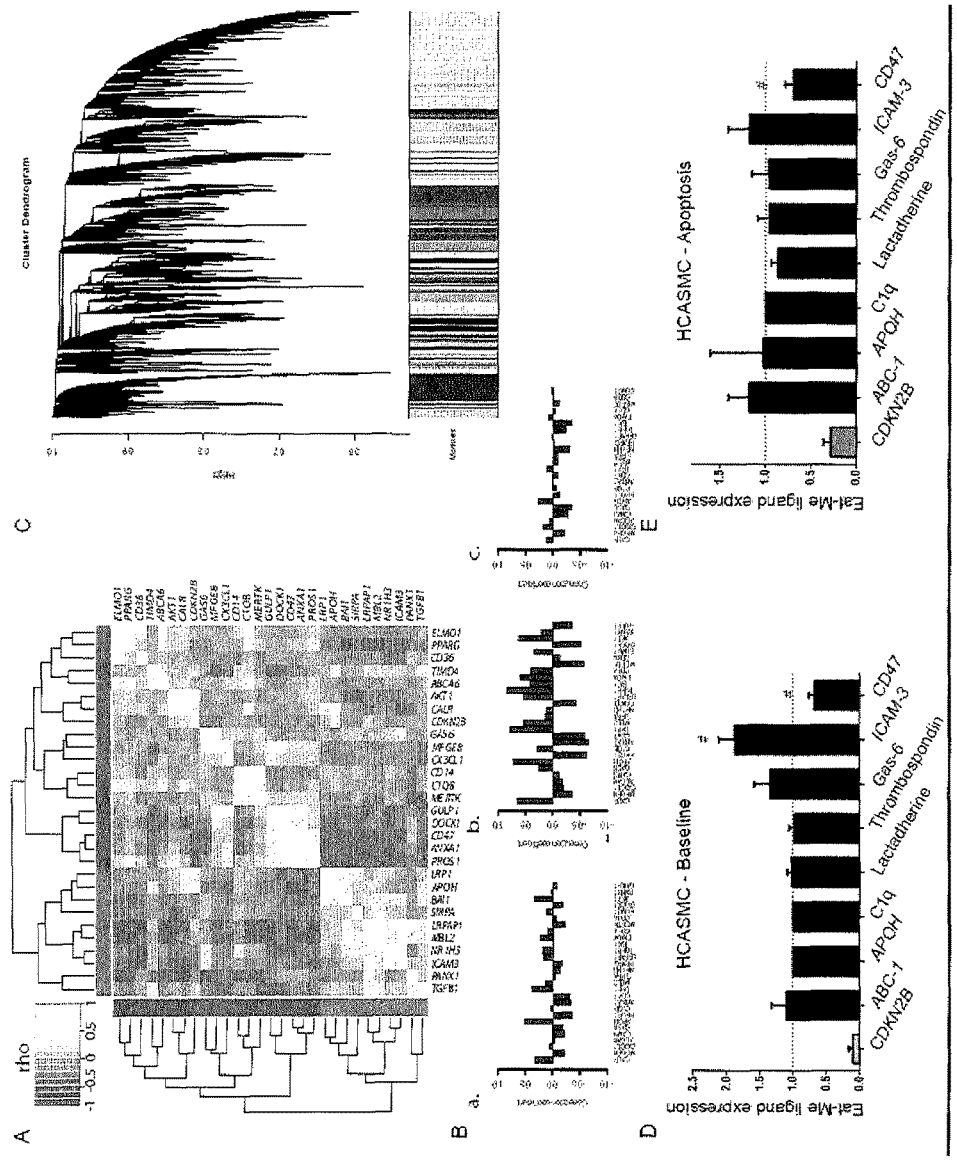

FIG. 8. Bioinformatics analysis of human atherosclerosis samples and evaluation of additional efferocytosis genes in HCASMC. (A) Topological relationship between CDKN2B and genes involved in efferocytosis in human coronary artery segments. Color bars correspond to module assignment. (B) Gene coexpression network cluster dendogram from human coronary artery segments. The network adjacency was calculated from topological overlap between all gene pairs represented in the expression data set. The dynamic tree cut algorithm was used to iteratively choose stable cluster sizes and partition the network into modules. (C) Correlation between CDKN2B expression and genes involved in efferocytosis in human coronary artery segments: (a) All samples; (b) samples without atherosclerotic lesions; (c) samples with atherosclerotic lesions. (D) Relative expression of several additional candidate efferocytosis genes in siCDKN2B HCASMC compared to siCont HCASMC at baseline (D) and during apoptosis (E).

Figure 3:
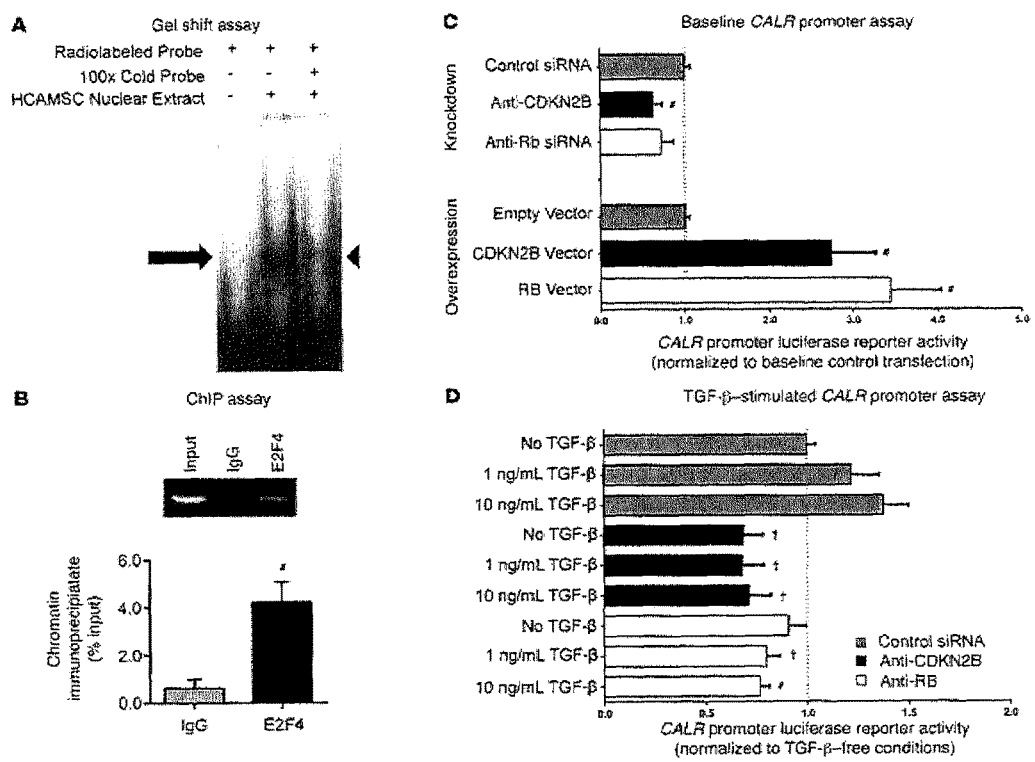
FIG. 3. Calreticulin expression is regulated by a cascade that includes CDKN2B and the RB/E2F4 axis. (A) EMSAs revealed specific binding of a γ-32P-ATP-labeled CALR promoter oligonucleotide probe containing the top predicted E2F4 binding site (from Table 1) to nuclear extracts harvested from HCASMCs. Arrow indicates shifted complex (lane 2), which was no longer observed in a competition reaction containing 0.100 unlabeled probe (lane 3, arrowhead). (B) ChIP studies revealed significant enrichment of E2F4 protein on the CALR promoter in human HCASMCs in vivo. (C) Overexpression and siRNA knockdown studies with dual-luciferase promoter reporter assays demonstrated that CALR expression is dependent on both CDKN2B and RB. (D) CALR expression was increased by TGF-β in a dose-dependent manner in control-transfected cells (gray bars). CDKN2B-deficient cells (black bars) displayed significantly less CALR reporter activity at baseline, and were unable to initiate CALR transcription in response to TGF-β. A similar pattern was observed in RB-deficient cells (white bars). P<0.01; +P<0.03.
Figure 9:
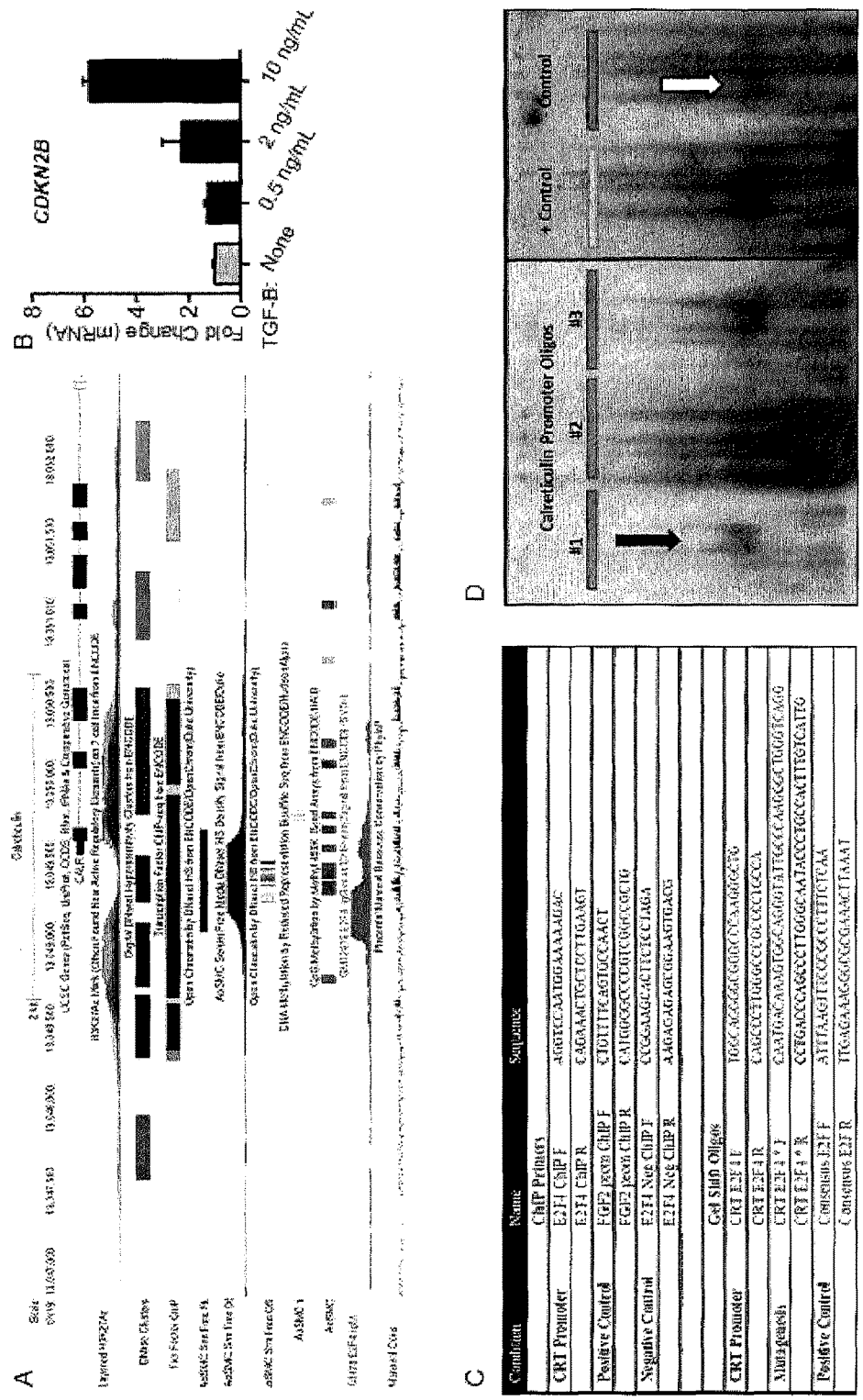

FIG. 9. Additional analysis of the CALR promoter. (A) Publically-available data from the UCSC genome browser reveals that the CALR promoter has an open chromatin pattern, DNase hypersensitivity sites, a consistent AoSMC DNA methylation pattern and published ChIP-seq data all of which suggest that E2F4 could regulate CALR expression in human SMCs. (B) Untransfected HCASMC increased their expression of CDKN2B in response to exogenous TGF-β stimulation in a pattern consistent with the luciferase reporter data shown in FIG. 3. (C) CALR promoter oligo sequences and ChiP primers employed in the EMSA and immunoprecipitation studies, respectively, described in FIG. 3. (D) Positive and negative control reactions employed in the EMSA experiments for FIG. 3.

Figure 10:
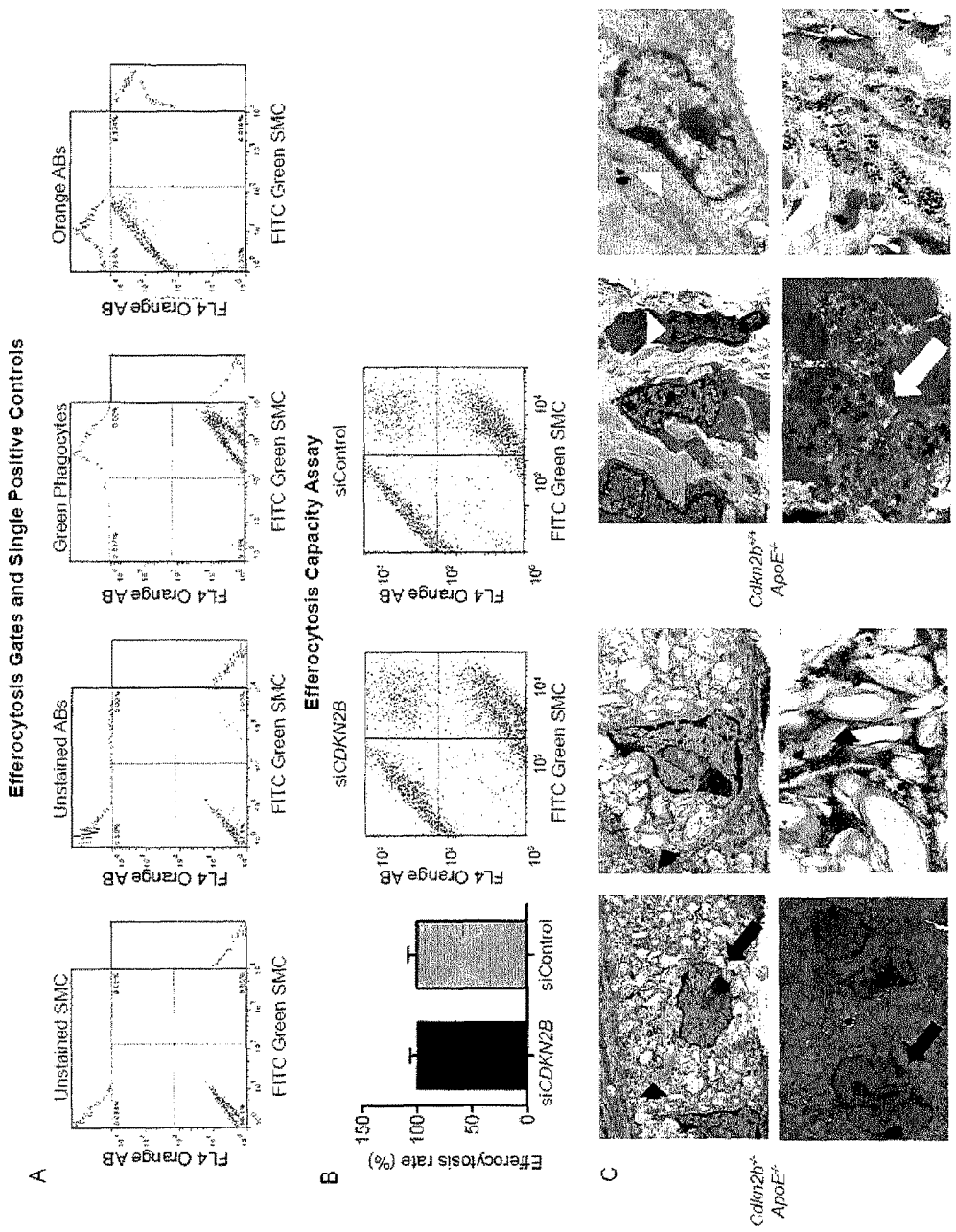

FIG. 10. CDKN2B does not alter the phagocytic capacity of the neighboring cell. (A) Control gates employed for all efferocytosis studies. (B) Although loss of CDKN2B rendered apoptotic cells resistant to efferocytosis, loss of CDKN2B in the neighboring, non-apoptotic HCASMC had no impact on its phagocytic capacity. Note that CDKN2B was undetectable in 'professional' phagocytes such as macrophages, in culture. (C) Additional examples of failed efferocytosis in vivo in Cdkn2b$^{-/-}$,ApoE$^{-/-}$ mice. Electron micrographs again reveal more frequent apoptosis and necrosis in Cdkn2b$^{-/-}$,ApoE$^{-/-}$ animals, with condensed chromatin and interruption of plasma membrane integrity (black arrows), along with a high burden of extracellular debris and ABs not associated with an adjacent macrophage (black arrowheads). Conversely, Cdkn2b$^{+/+}$,ApoE$^{-/-}$ control mice displayed smoothly outlined nuclei with normal heterochromatin patterns, normal sized mitochondria and intact plasma membranes (white arrowheads). These plaques also routinely displayed macrophages which had ingested numerous ABs, suggestive of intact efferocytosis.

Figure 11:
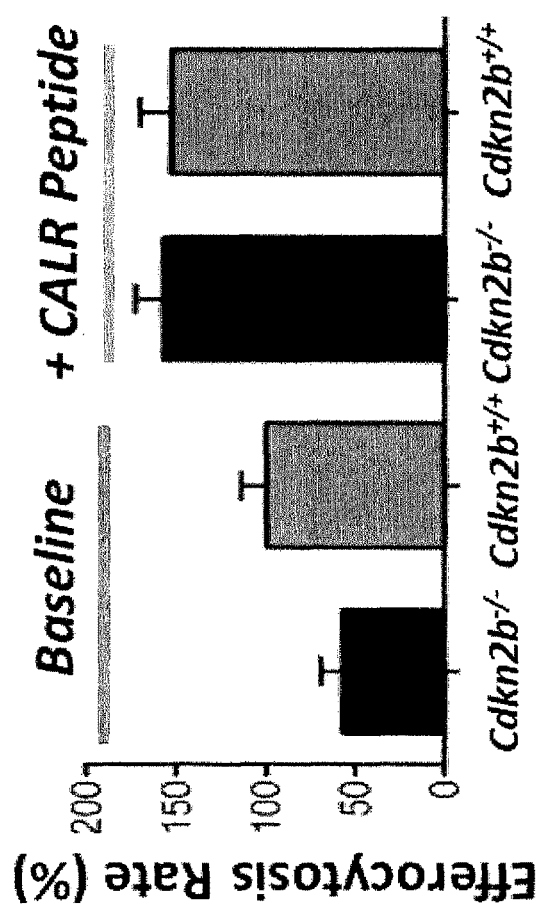

FIG. 11. Efferocytosis can be normalized in vitro. The Cdkn2b-dependent impairment in efferocytosis (left) can be fully reversed with the exogenous application of Calr peptide (right).

Figure 12:
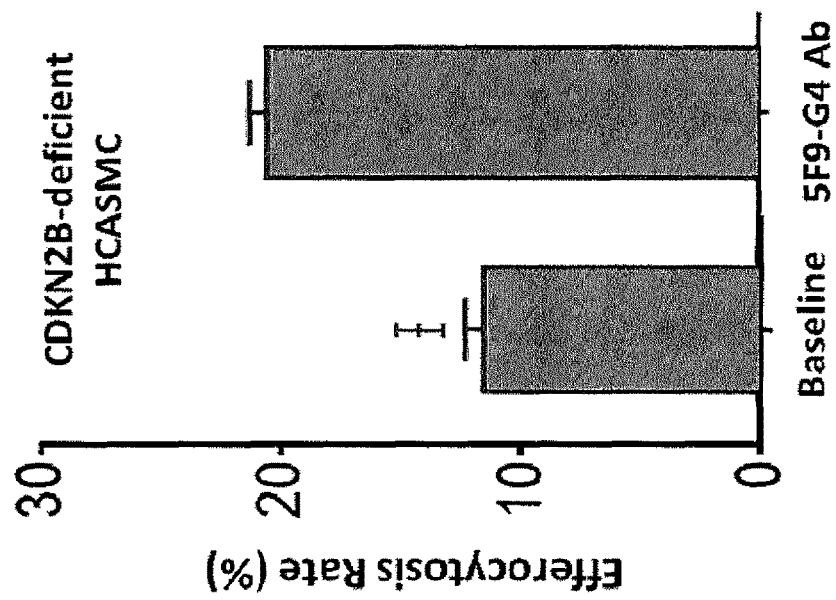

FIG. 12: Anti-CD47 Abs stimulate efferocytosis of CDKN2B-deficient SMCs. Hu5F9-G4 induces a ~72% increase in phagocytosis of SMCs by Mϕ's.

Figure 13:
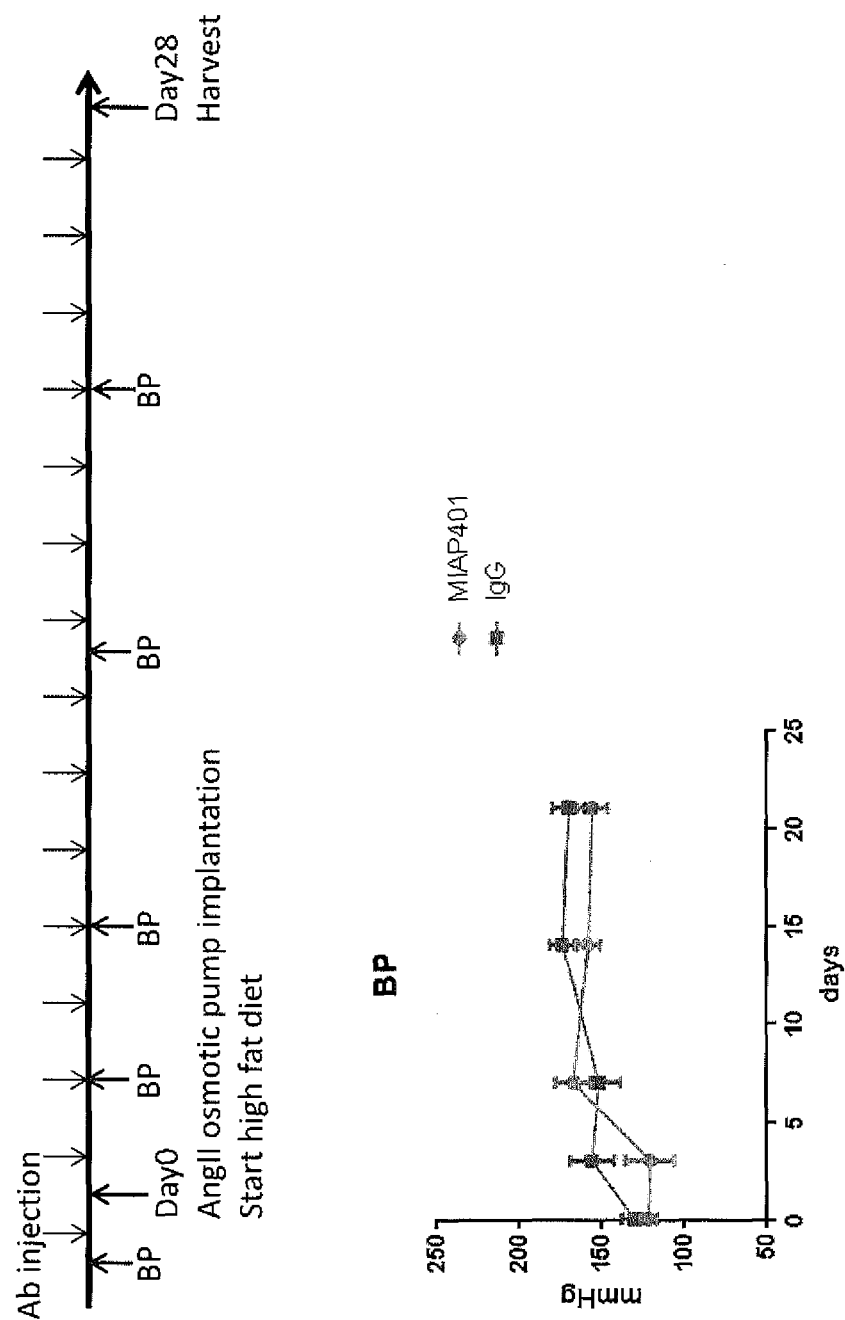

FIG. 13. Overview of atherosclerosis prevention study, showing timeline for anti-Cd47 Ab injection, blood pressure measurement, and high fat diet administration (top). Blood pressure changes over time during the treatment period (bottom).

Figure 14:
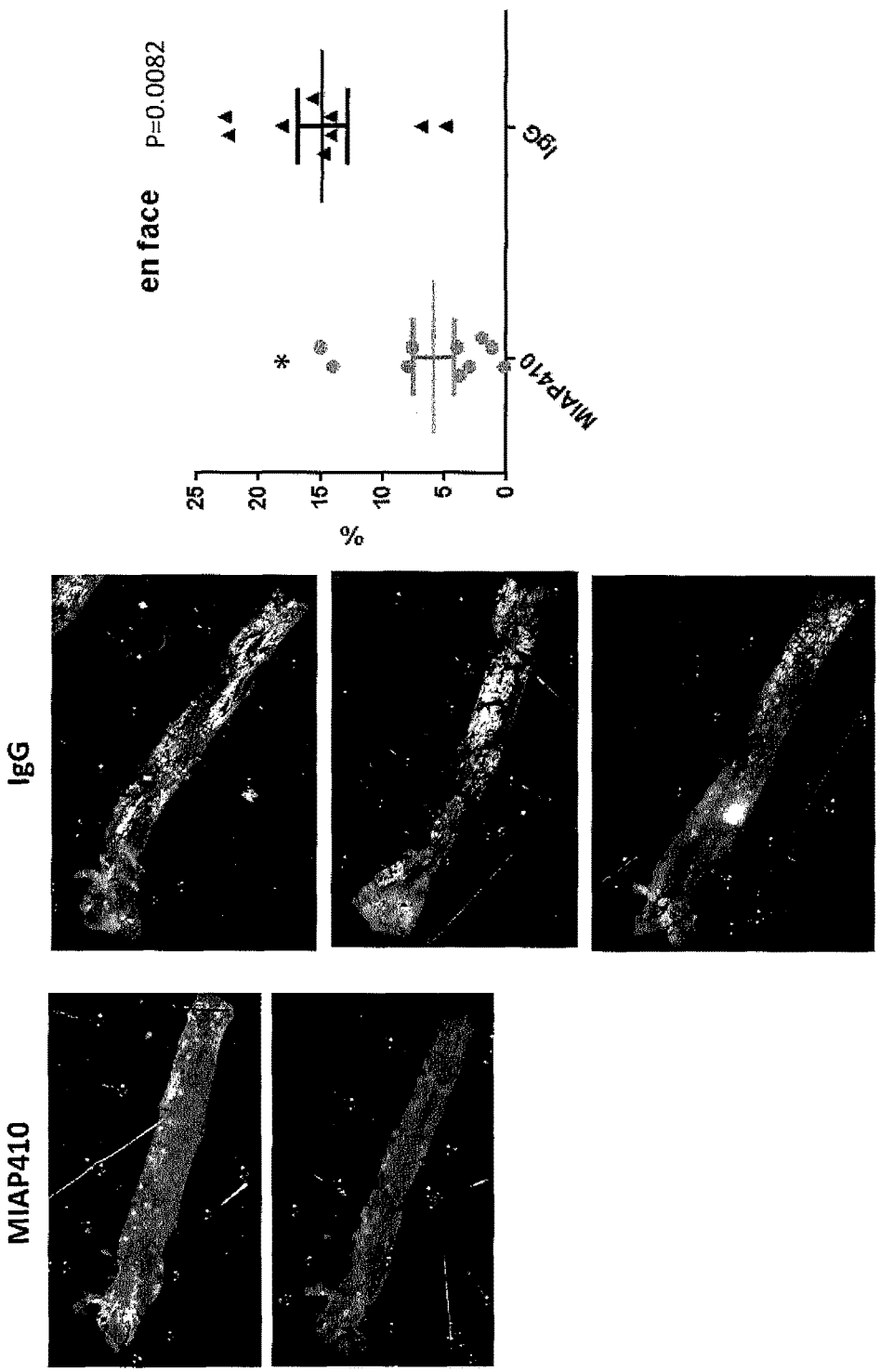

FIG. 14. Atherosclerotic plaque in the thoracic aorta is reduced by anti-CD47 Ab administration. Thoracic aortae from mice treated with anti-CD47 Ab (MIAP410) or control Ab (IgG) were harvested and pinned. Atherosclerotic plaque (white) area was quantified under low power microscopy in a blinded fashion. The percentage of the aortic vessel area covered by atherosclerotic plaque was quantified for each animal and is shown to be significantly reduced in animals which received anti-CD47 Ab.

Figure 15:
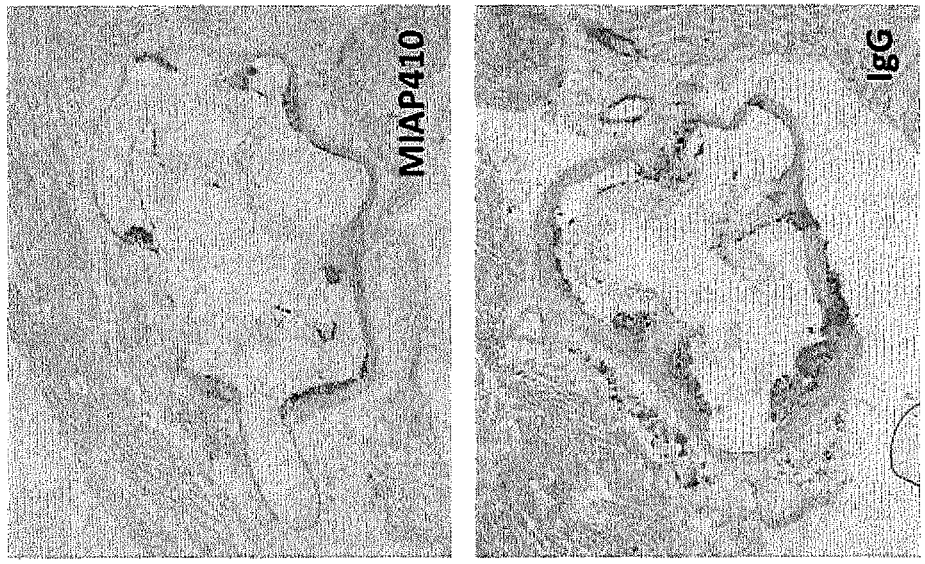
Figure 15:
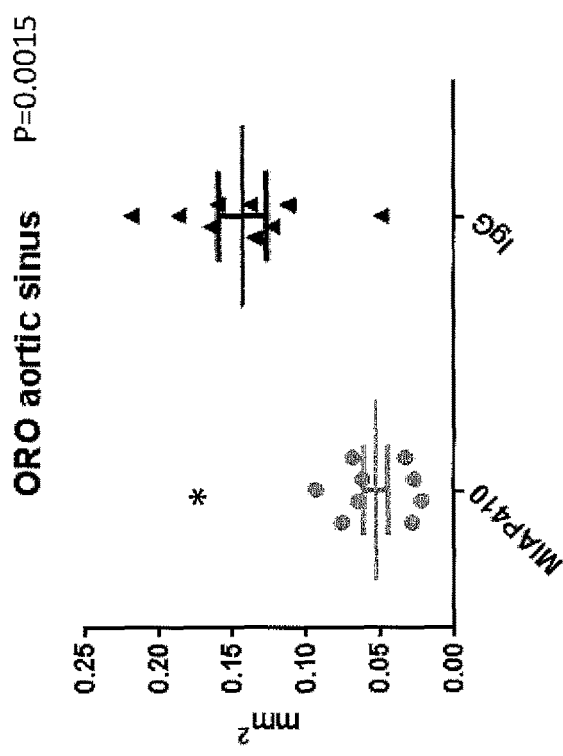

FIG. 15. Atherosclerotic plaque in the aortic sinus is reduced by anti-CD47 Ab administration. The aortic sinus from mice treated with anti-CD47 Ab (MIAP410) or control Ab (IgG) were harvested and sectioned after perfusion fixation. Atherosclerotic plaque was stained by oil-red-O and the affected area (in red) was quantified under low power microscopy in a blinded fashion. The absolute area of the aortic sinus affected by atherosclerotic plaque was quantified for each animal and is shown to be significantly reduced in animals which received anti-CD47 Ab.

Figure 16:
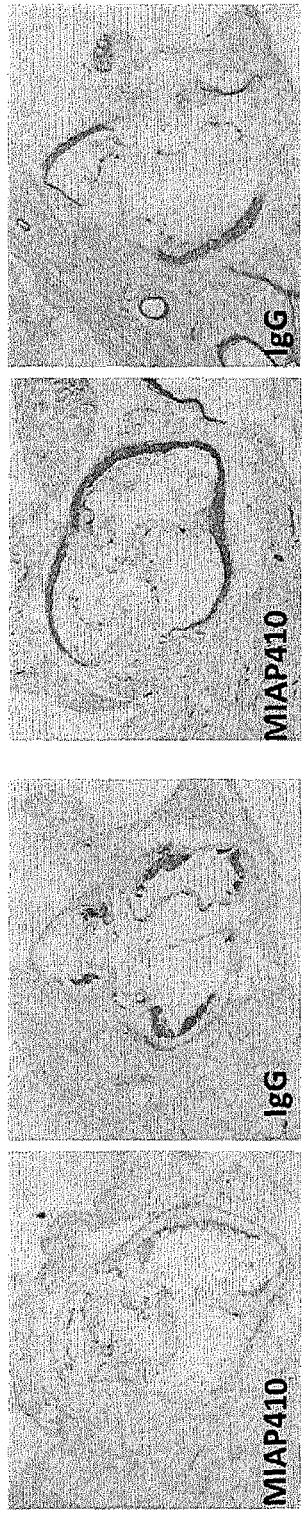
Figure 16:
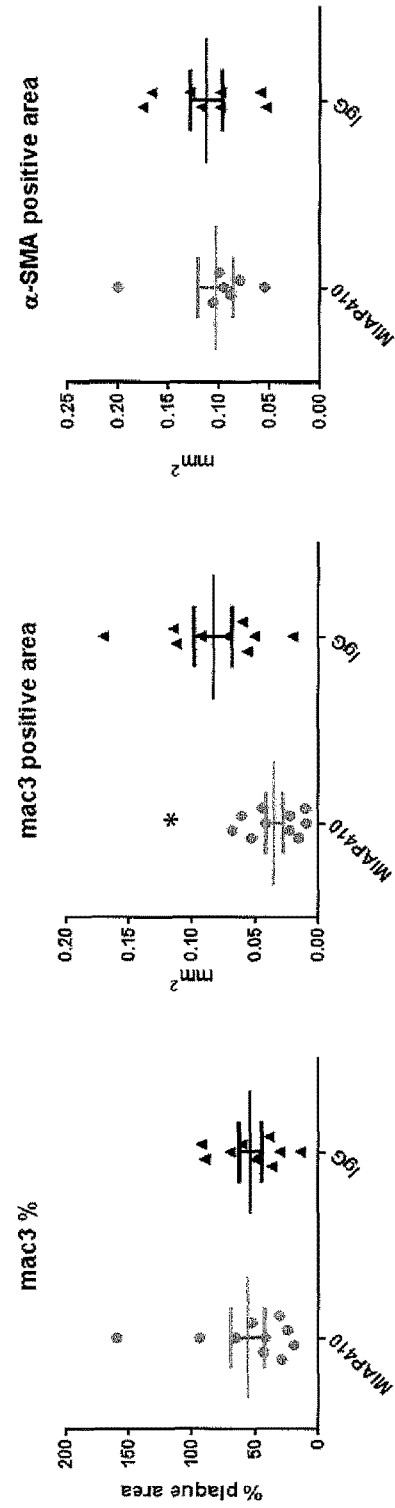

FIG. 16. Representative immunohistochemical stains of the aortic sinus sections taken from mice treated with anti-CD47 Ab (MIAP410) or control Ab (IgG) reveal that anti-CD47 Ab therapy does not affect SMC content, as assessed by alpha-SMA staining. The absolute macrophage content (quantified by staining for Mac-3) shows that the total macrophage content is reduced in mice receiving anti-CD47 Ab (MIAP410) therapy, however the relative content is no different, when normalized to total lesion size.

DETAILED DESCRIPTION OF THE INVENTION

The present invention relates to methods of treating a subject for atherosclerosis, including conditions such as CAD, peripheral artery disease (PAD) and cerebrovascular disease, by administering an agent that increases efferocytosis of cellular components of atherosclerotic plaque, including the efferocytosis of apoptotic smooth muscle cells.

In some embodiments, the subject is homozygous or heterozygous for a 9p21 risk allele. In some embodiments, the agent that increases efferocytosis provides for one or more of the following activities: reduces the binding of CD47 to SIRPα; increases or mimics the activity of calreticulin, including binding of calreticulin to LRP; or increases expression of CDKN2B.

Coronary artery disease (CAD): is a narrowing or blockage of the arteries and vessels that provide oxygen and nutrients to the heart. It is caused by atherosclerosis, an accumulation of fatty materials on the inner linings of arteries. The resulting blockage restricts blood flow to the heart. When the blood flow is completely cut off, the result is a heart attack. CAD is the leading cause of death for both men and women in the United States.

Atherosclerosis (also referred to as arteriosclerosis, atheromatous vascular disease, arterial occlusive disease) as used herein, refers to a cardiovascular disease characterized by plaque accumulation on vessel walls and vascular inflammation. The plaque consists of accumulated intracellular and extracellular lipids, smooth muscle cells, connective tissue, inflammatory cells, and glycosaminoglycans. Inflammation occurs in combination with lipid accumulation in the vessel wall, and vascular inflammation is with the hallmark of atherosclerosis disease process.

Myocardial infarction is an ischemic myocardial necrosis usually resulting from abrupt reduction in coronary blood flow to a segment of myocardium. In the great majority of patients with acute MI, an acute thrombus, often associated with plaque rupture, occludes the artery that supplies the damaged area. Plaque rupture occurs generally in vessels previously partially obstructed by an atherosclerotic plaque enriched in inflammatory cells. Altered platelet function induced by endothelial dysfunction and vascular inflammation in the atherosclerotic plaque presumably contributes to thrombogenesis. Myocardial infarction can be classified into ST-elevation and non-ST elevation MI (also referred to as unstable angina). In both forms of myocardial infarction, there is myocardial necrosis. In ST-elevation myocardial infraction there is transmural myocardial injury which leads to ST-elevations on electrocardiogram. In non-ST elevation myocardial infarction, the injury is sub-endocardial and is not associated with ST segment elevation on electrocardiogram. Myocardial infarction (both ST and non-ST elevation) represents an unstable form of atherosclerotic cardiovascular disease. Acute coronary syndrome encompasses all forms of unstable coronary artery disease. Heart failure can occur as a result of myocardial dysfunction caused by myocardial infraction.

Angina refers to chest pain or discomfort resulting from inadequate blood flow to the heart. Angina can be a symptom of atherosclerotic cardiovascular disease. Angina may be classified as stable, which follows a regular chronic pattern of symptoms, unlike the unstable forms of atherosclerotic vascular disease. The pathophysiological basis of stable atherosclerotic cardiovascular disease is also complicated but is biologically distinct from the unstable form. Generally stable angina is not myocardial necrosis.

9p21 Risk. As used herein, the term "an individual carrying at least one 9p21 risk factor" refers to humans in which one or more risk alleles at the 9p21 locus are present in the genome. Such individuals have been shown to have an increased risk of: early onset myocardial infarction, abdominal aortic aneurysm, stroke, peripheral artery disease, and myocardial infarction/coronary heart disease. This risk is independent of traditional risk factors, including diabetes, hypertension, cholesterol, and obesity. See, for example, Helgadottir et al. Science. 2007; 316(5830):1491-1493; Helgadottir et al. Nat Genet. 2008; 40(2):217-224; Palomaki et al. JAMA. 2010; 303(7):648-656; and Roberts et al. Curr Opin Cardiol. 2008; 23:629-633, each herein specifically incorporated by reference.

The 9p21 locus is in tight LD (linkage disequilibrium), and a number of single nucleotide polymorphisms (SNP) markers have been shown to be useful in diagnosis. Representative SNPs include without limitation rs10757278; rs3217992; rs4977574; rs1333049; rs10757274; rs2383206; rs2383207; Rs3217989; rs1333040; rs2383207; rs10116277; rs7044859; rs1292136; rs7865618; rs1333045; rs9632884; rs10757272; rs4977574; rs2891168; rs6475606; rs1333048; rs1333049; Rs1333045; etc.

Efferocytosis. The process by which professional and nonprofessional phagocytes dispose of apoptotic cells in a rapid and efficient manner. Efferocytosis involves a number of molecules, including ligands on the apoptotic cells, e.g. phosphatidylserine; receptors on the efferocyte; soluble ligand-receptor bridging molecules; and so-called "find-me" and "don't-eat-me" molecules, e.g., lysosphospholipids and CD47, the expression of which by dying cells is altered to attract nearby phagocytes. By clearing apoptotic cells at a relatively early stage of cell death, when the cell plasma and organelle membranes are still intact, postapoptotic, or "secondary", necrosis is prevented. Prevention of cellular necrosis, in turn, prevents the release of potentially damaging intracellular molecules into the extracellular milieu, including molecules that can stimulate inflammatory, proatherosclerotic and/or autoimmune responses.

The efficiency of efferocytic clearance in atherosclerotic lesions plays a key role in disease development. Efferocytosis is known to be impaired in human atherosclerotic plaque. A prominent feature of advanced atherosclerotic lesions is the necrotic core, or lipid core, which is a collection of dead and necrotic macrophages surrounded by inflammatory cells. Necrotic cores are thought to be a major feature responsible for plaque "vulnerability", i.e., plaques capable of undergoing disruption and triggering acute luminal thrombosis. Plaque disruption and acute thrombosis are the events that trigger acute coronary syndromes, including myocardial infarction, unstable angina, sudden cardiac death, and stroke.

By "manipulating efferocytosis" is meant an up-regulation or a down-regulation in efferocytosis of a targeted cell, e.g. apoptotic SMC, by at least about 10%, or up to 20%, or 50%, or 70% or 80% or up to about 90% compared to level of efferocytosis observed in absence of intervention.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells. However, "non-professional" cells are also known to participate in efferocytosis, such as neighboring SMCs in the blood vessel wall.

"Treatment", "treating", "treat" and the like are used herein to generally refer to obtaining a desired pharmacologic and/or physiologic effect. The effect can be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom. Those in need of treatment include individuals already diagnosed with CAD, e.g. atherosclerosis, as well as those in which the disease is to be prevented.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

An "effective amount" is an amount sufficient to effect beneficial or desired clinical results. An effective amount can be administered in one or more administrations. For purposes of this invention, an effective amount of an anti-CD47 agent is an amount that is sufficient to palliate, ameliorate, stabilize, reverse, prevent, slow or delay the progression of the disease state, e.g. atherosclerosis or atherosclerotic plaque, by increasing phagocytosis of a target cell. For example, in an animal model the percent of aortic surface area with atherosclerotic plaque may be reduced 25%, 50%, 75% or more relative to a control treated animal. Similar effects may be obtained with indicia appropriate for human patients, including without limitation C-reactive protein [CRP] and fibrinogen; lipoprotein-associated phospholipase A2 [Lp-PLA2] and myeloperoxidase [MPO]; growth differentiation factor-15 [GDF-15]) inflammatory markers; ambulatory arterial stiffness, IVUS imaging, and the like. See, for example Krintus et al. (2013) Crit Rev Clin Lab Sci. 11:1-17; Kollias et al. (2012) Atherosclerosis 224(2):291-301; and Kollias et al. (2011) Int. J. Cardiovasc. Imaging 27(2):225-37, each herein specifically incorporated by reference.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations. The definition also includes sample that have been enriched for particular types of molecules, e.g., nucleic acids, polypeptides, etc.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides; high affinity binding of a SIRPα polypeptide to CD47; etc.) In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 (i.e., anti-CD47 agents), or that otherwise block the interaction between CD47 and SIRPα, agents that bind to calreticulin or its LRP receptor, etc.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural protein.

A "fusion" polypeptide is a polypeptide comprising a polypeptide or portion (e.g., one or more domains) thereof fused or bonded to heterologous polypeptide. A fusion soluble CRT protein, for example, will share at least one biological property in common with a native sequence soluble CRT polypeptide. Examples of fusion polypeptides include immunoadhesins, as described above, which combine a portion of the polypeptide of interest with an immunoglobulin sequence, and epitope tagged polypeptides, which comprise a soluble polypeptide of interest or portion thereof fused to a "tag polypeptide". The tag polypeptide has enough residues to provide an epitope against which an antibody can be made, yet is short enough such that it does not interfere with biological activity of the polypeptide of interest. Suitable tag polypeptides generally have at least six amino acid residues and usually between about 6-60 amino acid residues.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications thereof. For example, derivatives and fusion of soluble CRT find use as CRT mimetic molecules.

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Cyclin-dependent kinase inhibitor 2B (CDKN2B) is also known as multiple tumor suppressor 2 (MTS-2) or p15INK4B. The Genbank refseq for the human mRNA has the accession number NM_004936 and the protein refseq has the accession number NP_004927. This gene lies adjacent to the tumor suppressor gene CDKN2A in a region that is frequently mutated and deleted in a wide variety of tumors.

CDKN2B forms a complex with CDK4 or CDK6, and prevents the activation of the CDK kinases by cyclin D, thus the encoded protein functions as a cell growth regulator that inhibits cell cycle G1 progression.

It is shown herein that decreased CDKN2B expression associated with 9p21 risk alleles impairs expression of calreticulin, a ligand required for activation of engulfment receptors on phagocytic cells. As a result, cdkn2B-deficient apoptotic bodies, e.g. apoptotic smooth muscle cells, are rendered resistant to efferocytosis and are not efficiently cleared by phagocytic cells. Agents that activate or upregulate CDKN2B expression are known in the art, including, for example, palbociclib (see Toogood et al. (2005) J Med Chem. 48(7):2388-406); 5-aza-2'-deoxycytidine in the absence or presence of phenylbutyrate (see Lemaire et al. (2004) *Leuk Lymphoma.* 45(1):147-54); hypoxia-inducible-factors-1a and −2a (see Aesoey et al. (2013) Endocr Rev, Vol. 34 (03_Meeting Abstracts): SUN-303; etc. Agents that activate or upregulate CDKN2B can be determined by screening methods as known in the art.

Calreticulin. Calreticulin is a multifunctional protein of 417 amino acids, molecular weight 48 kDa, that binds $Ca^{2+}$ ions, rendering it inactive. The $Ca^{2+}$ is bound with low affinity, but high capacity, and can be released on a signal. Calreticulin can be located in storage compartments associated with the endoplasmic reticulum, where it binds to misfolded proteins and prevents them from being exported to the Golgi apparatus. Calreticulin is also found in the nucleus, suggesting that it may have a role in transcription regulation. Calreticulin binds to the synthetic peptide KLGFFKR, which is almost identical to an amino acid sequence in the DNA-binding domain of the superfamily of nuclear receptors. The gene symbol for calreticulin is CALR, and the human sequences may be accessed at Pubmed as follows: Protein Accession# NP_004334; Nucleotide Accession#: NM_004343.

Calreticulin on the surface of apoptotic cells serves as a recognition and clearance ligand by activating the internalization receptor LRP on the responding phagocyte cell surface. The surface expression of calreticulin increases and calreticulin was redistributed during apoptosis, possibly enhancing stimulation of LRP on the phagocyte.

The low density lipoprotein receptor-related protein (LRP) is a 4,544-amino acid protein containing a single transmembrane segment, with a high degree of sequence identity to the LDL receptor. The human genetic sequences may be accessed at Pubmed as follows: Nucleotide Accession#: NM_002332.2 GI:126012561.

Agents that specifically bind to calreticulin (CRT) are of interest as agonists for enhancing the pro-phagocytic activity of CRT. CRT binding agents useful in the methods of the invention include analogs, derivatives and fragments of the original specific binding member, e.g. Fab fragments of antibodies, etc. Calreticulin "mimetics" and "agonists" include molecules that function similarly to or potentiate CRT by binding and activating LRP receptor. Molecules useful as CRT mimetics include derivatives, variants, and biologically active fragments of naturally occurring CRT. Molecules useful as agonists include antibodies and other agents that act to enhance the pro-phagocytic activity of CRT.

Fragments of soluble CRT, particularly biologically active fragments and/or fragments corresponding to functional domains, are of interest. Fragments of interest will typically be at least about 10 aa to at least about 15 aa in length, usually at least about 50 aa in length, but will usually not exceed about 142 aa in length, where the fragment will have a stretch of amino acids that is identical to CRT. A fragment "at least 20 aa in length," for example, is intended to include 20 or more contiguous amino acids from, for example, the polypeptide encoded by a cDNA for CRT. In this context "about" includes the particularly recited value or a value larger or smaller by several (5, 4, 3, 2, or 1) amino acids.

In vitro assays for calreticulin biological activity include, e.g. phagocytosis of porcine cells by human macrophages, binding to LRP, etc. A candidate agent useful as a calreticulin agonist mimetic results in the down regulation of phagocytosis by at least about 10%, at least about 20%, at least about 50%, at least about 70%, at least about 80%, or up to about 90% compared to level of phagocytosis observed in absence of candidate agent.

CD47, also known as integrin associated protein (IAP,) is a 50 kDa membrane receptor that has extracellular N-terminal IgV domain, five transmembrane domains, and a short C-terminal intracellular tail transmembrane, belonging to the immunoglobulin superfamily, with interacts with integrins, most commonly integrin αvβ3, thrombospondin-1 (TSP-1) and signal-regulatory protein alpha (SIRPα). The reference sequence for the human mRNA has the Genbank accession number NM_001025079, and the protein reference sequence is NP_001768.

The CD47/SIRPα interaction leads to bidirectional signaling, resulting in different cell-to-cell responses including inhibition of phagocytosis, stimulation of cell-cell fusion, and T-cell activation As used herein, the term "anti-CD47 agent" refers to any agent that reduces the binding of CD47 (e.g., on an affected cell) to SIRPα (e.g., on a phagocytic cell). In some embodiments the anti-CD47 agent does not interfere or bind to the regions of CD47 that bind to thrombospondin. In some embodiments, the anti-CD47 agent does not activate CD47 upon binding. When CD47 is activated, a process akin to apoptosis (i.e., programmed cell death) occurs (Manna and Frazier, Cancer Research, 64, 1026-1036, Feb. 1, 2004). Thus, in some embodiments, the anti-CD47 agent does not directly induce cell death of a CD47-expressing cell.

Non-limiting examples of suitable anti-CD47 reagents include high affinity SIRPα reagents, anti-SIRPα antibodies, and anti-CD47 antibodies or antibody fragments. In some embodiments, a suitable anti-CD47 agent (e.g. an anti-CD47 antibody, a high affinity SIRPα reagent, etc.) specifically binds CD47 to reduce the binding of CD47 to SIRPα. In some embodiments, a suitable anti-CD47 agent (e.g., an anti-SIRPα antibody, etc.) specifically binds SIRPα to reduce the binding of CD47 to SIRPα. A suitable anti-CD47 agent that binds SIRPα does not activate SIRPα (e.g., in the SIRPα-expressing phagocytic cell).

The efficacy of a suitable anti-CD47 agent can be assessed by assaying the agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 160%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In one embodiment of the invention, the anti-CD47 agent, or a pharmaceutical composition comprising the agent, is provided in an amount effective to detectably inhibit the binding of CD47 to SIRPα present on the surface of phagocytic cells. The effective amount is determined via empirical testing routine in the art, for example in a biological sample taken from an infected individual. The effective amount may vary depending on the number of cells being targeted, the location of the cells, and factors specific to the subject.

High affinity SIRPα reagent. In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. In other embodiments, the second polypeptide is any suitable polypeptide that is substantially similar to Fc, e.g., providing increased size, multimerization domains, and/or additional binding or interaction with Ig molecules.

A suitable high affinity SIRPα reagent reduces (e.g., blocks, prevents, etc.) the interaction between the native proteins SIRPα and CD47. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 Antibodies.

In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference).

Anti-SIRPα Antibodies.

In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of infected cells over non-infected cells. Those cells that express higher levels of CD47 (e.g., infected cells) relative to other cells (non-infected cells) will be preferentially phagocytosed. Thus, a suitable anti-SIRPα antibody specifically binds SIRPα without activating/stimulating enough of a signaling response to inhibit phagocytosis.

Suitable antibodies include fully human, humanized or chimeric versions of such antibodies. Humanized antibodies are especially useful for in vivo applications in humans due to their low antigenicity. Similarly caninized, felinized, etc antibodies are especially useful for applications in dogs, cats, and other species respectively.

Methods

Methods are provided for treating or reducing atherosclerosis by administering an agent to an individual that increases efferocytosis of cellular components of coronary or extracardiac plaque, including the efferocytosis of apoptotic smooth muscle cells. In some embodiments, the individual is homozygous or heterozygous for a 9p21 risk allele. In some embodiments, the agent that increases efferocytosis provides for one or more of the following activities: reduces the binding of CD47 to SIRPα; increases or mimics the activity of calreticulin, including binding of calreticulin to LRP; or increases expression of CDKN2B. Such methods include administering to a subject in need of treatment a therapeutically effective amount or an effective dose of an efferocytosis stimulating agent, including without limitation combinations of the agent with another drug. Methods of administration to the cardiovascular system are of interest, although oral formulations may also find use.

Effective doses of the therapeutic entity of the present invention vary depending upon many different factors, including the nature of the agent, means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage can range from about 0.0001 to 500 mg/kg, and more usually 0.01 to 100 mg/kg, of the host body weight. For example dosages can be 1 mg/kg body weight or 10 mg/kg body weight or within the range of 1-50 mg/kg. The dosage may be adjusted for the molecular weight of the reagent. An exemplary treatment regime entails administration daily, semi-weekly, weekly, once every two weeks, once a month, etc. In another example, treatment can be given as a continuous infusion. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient. It will be understood by one of skill in the art that such guidelines will be adjusted for the molecular weight of the active agent, e.g. in the use of polypeptide fragments, in the use of antibody conjugates, in the use of high affinity SIRPα reagents, etc. The dosage may also be varied for localized administration, e.g. intranasal, inhalation, etc., or for systemic administration, e.g. i.m., i.p., i.v., and the like.

For the treatment of disease, the appropriate dosage of the agent will depend on the severity and course of the disease, whether the agent is administered for preventive purposes, previous therapy, the patient's clinical history and response to the antibody, and the discretion of the attending physician. The agent is suitably administered to the patient at one time or over a series of treatments.

Suitable agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an efferocytosis stimulating agent includes use in combination with another therapeutic agent, e.g., drugs useful in the treatment of atherosclerosis. Such combinations may include, without limitation, statins. Statins are inhibitors of HMG-CoA reductase enzyme. These agents are described in detail; for example, mevastatin and related compounds as disclosed in U.S. Pat. No. 3,983,140; lovastatin (mevinolin) and related compounds as disclosed in U.S. Pat. No. 4,231,938; pravastatin and related compounds as disclosed in U.S. Pat. No. 4,346,227; simvastatin and related compounds as disclosed in U.S. Pat. Nos. 4,448,784 and 4,450,171; fluvastatin and related compounds as disclosed in U.S. Pat. No. 5,354,772; atorvastatin and related compounds as disclosed in U.S. Pat. Nos. 4,681,893, 5,273,995 and 5,969,156; and cerivastatin and related compounds as disclosed in U.S. Pat. Nos. 5,006,530 and 5,177,080. Additional agents and compounds are disclosed in U.S. Pat. Nos. 5,208,258, 5,130,306, 5,116,870, 5,049,696, RE 36,481, and RE 36,520. Statins include the salts and/or ester thereof.

Other drugs useful in combination include, for example, fibrates such as gemfibrozil, fenofibrate, etc.; niacin; zetia; bile acid sequestrants, e.g. cholestyramine, colestipol, colesevelam; lovaza, vascepa; drugs to reduce hypertension, etc.

Therapeutic formulations comprising one or more agents of the invention are prepared for storage by mixing the agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the agent to be administered will be governed by such considerations, and is the minimum amount necessary to treat or prevent atherosclerosis.

The agent can be administered by any suitable means, including topical, oral, parenteral, subcutaneous, intraperitoneal, intrapulmonary, and intranasal. Parenteral infusions include intramuscular, intravenous, intraarterial, intraperitoneal, intrathecal or subcutaneous administration. In addition, the agent can be suitably administered by pulse infusion, particularly with declining doses of the agent.

The agent need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

An agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macro-molecules such as proteins, polysaccharides such as chitosan, polylactic acids, polyglycolic acids and copolymers (such as latex functionalized Sepharose™ agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-CD47 agent by non-covalent associations, such as non-covalent bonding or by encapsulation. The nature of the carrier can be either soluble or insoluble for purposes of the invention. Those skilled in the art will know of other suitable carriers for binding anti-CD47 agents, or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethyl-benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the anti-CD47 agent through an acceptable chemical linker or chelation carrier. Positron emitting moieties for use in the present invention include $^{18}$F, which can be easily conjugated by a fluorination reaction with the agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Genetic Screening

In one aspect of the present invention, an individual is tested for the presence of a 9p21 risk allele prior to treatment. Such methods comprise an analysis of genomic DNA in an individual for a 9p21 allele that confers an increased susceptibility to atherosclerosis. Individuals are screened by analyzing their genomic sequence at 9p21, e.g. rs10757278 or rs1333049 or another representative 9p21 SNP sequences for the presence of a predisposing allele, as compared to a normal sequence.

A number of methods are used for determining the presence of a predisposing variant in an individual. Genomic DNA is isolated from the individual or individuals that are to be tested. DNA can be isolated from any nucleated cellular source such as blood, hair shafts, saliva, mucous, biopsy, feces, etc. Methods using PCR amplification can be performed on the DNA from a single cell, although it is convenient to use at least about $10^5$ cells. Where large amounts of DNA are available, the genomic DNA is used directly. Alternatively, the region of interest is cloned into a suitable vector and grown in sufficient quantity for analysis, or amplified by conventional techniques. Of particular interest is the use of the polymerase chain reaction (PCR) to amplify the DNA that lies between two specific primers. The use of the polymerase chain reaction is described in Saiki et al. (1985) *Science* 239:487, and a review of current techniques may be found in McPherson et al. (2000) PCR (Basics: From Background to Bench) Springer Verlag; ISBN: 0387916008. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^3H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Primer pairs are selected from the genomic sequence using conventional criteria for selection. The primers in a pair will hybridize to opposite strands, and will collectively flank the region of interest. The primers will hybridize to the complementary sequence under stringent conditions, and will generally be at least about 16 nt in length, and may be 20, 25 or 30 nucleotides in length. The primers will be selected to amplify the specific region suspected of containing the predisposing mutation. Typically the length of the amplified fragment will be selected so as to allow discrimination between repeats of 3 to 7 units. Multiplex amplification may be performed in which several sets of primers are combined in the same reaction tube, in order to analyze multiple exons simultaneously. Each primer may be conjugated to a different label.

The exact composition of the primer sequences are not critical to the invention, but they must hybridize to the flanking sequences under stringent conditions. Criteria for selection of amplification primers are as previously discussed. To maximize the resolution of size differences at the locus, it is preferable to choose a primer sequence that is close to the SNP sequence, such that the total amplification product is at least about 30, more usually at least about 50, preferably at least about 100 or 200 nucleotides in length, which will vary with the number of repeats that are present, to not more than about 500 nucleotides in length. The number of repeats has been found to be polymorphic, as previously described, thereby generating individual differences in the length of DNA that lies between the amplification primers. Conveniently, a detectable label is included in the amplification reaction. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products can be size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. (1991) Science 254:59-74. The automated sequencer is particularly useful with multiplex amplification or pooled products of separate PCR reactions. Capillary electrophoresis may also be used for fractionation. A review of capillary electrophoresis may be found in Landers, et al. (1993) BioTechniques 14:98-111. The size of the amplification product is proportional to the number of repeats (n) that are present at the locus specified by the primers. The size will be polymorphic in the population, and is therefore an allelic marker for that locus. The amplified or cloned fragment is alternatively sequenced by various high methods known in the art.

The presence of a predisposing risk allele is indicative that an individual is at increased risk of developing atherosclerosis and may benefit from treatment by the methods of the invention, although the methods can additionally find use in individuals without a 9p21 genetic risk factor. The diagnosis of a disease predisposition allows the affected individual to seek early treatment of potential lesions, and to avoid activities that increase risk for cardiovascular disease.

Drug Screening

Screening assays identify compounds that modulate the expression or activity of proteins involved in efferocytosis, including without limitation CDKN2B, calreticulin, CD47, SIRPα, etc. An efferocytosis stimulating agent can, for example, act as the basis for amelioration of such cardiovascular diseases as atherosclerosis, ischemia/reperfusion, hypertension, restenosis, and arterial inflammation. Such compounds may include, but are not limited to peptides, antibodies, or small organic or inorganic compounds. Methods for the identification of such compounds are described below.

Cell- and animal-based systems can act as models for cardiovascular disease and are useful in such drug screening. The animal- and cell-based models may be used to identify drugs, pharmaceuticals, therapies and interventions that are effective in treating cardiovascular disease. In addition, such animal models may be used to determine the $LD_{50}$ and the $ED_{50}$ in animal subjects, and such data can be used to determine the in vivo efficacy of potential cardiovascular disease treatments. Animal-based model systems of cardiovascular disease may include, but are not limited to, non-recombinant and engineered transgenic animals. Non-recombinant, non-genetic animal models of atherosclerosis may include, for example, pig, rabbit, or rat models in which the animal has been exposed to either chemical wounding through dietary supplementation of LDL, or mechanical wounding through balloon catheter angioplasty, for example. Additionally, animal models exhibiting cardiovascular disease symptoms may be engineered by utilizing, for example, smooth muscle cell marking, knockouts of CDKN2B, etc. gene sequences in conjunction with techniques for producing transgenic animals that are well known to those of skill in the art. For example, target gene sequences may be introduced into, and knocked out or overexpressed in the genome of the animal of interest. Animals of any species, including, but not limited to, mice, rats, rabbits, guinea pigs, pigs, micro-pigs, goats, and non-human primates, e.g., baboons, monkeys, and chimpanzees may be used to generate cardiovascular disease animal models.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148-6152); gene targeting in embryonic stem cells (Thompson et al., 1989, Cell 56:313-321); electroporation of embryos (Lo, 1983, Mol Cell. Biol. 3:1803-1814); and sperm-mediated gene transfer (Lavitrano et al., 1989, Cell 57:717-723); etc.

Specific cell types within the animals may be analyzed and assayed for cellular phenotypes characteristic of cardiovascular disease. In the case of monocytes, such phenotypes may include but are not limited to increases in rates of LDL uptake, adhesion to endothelial cells, transmigration, foam cell formation, fatty streak formation, and production of foam cell specific products. Further, such cellular phenotypes may include a particular cell type's fingerprint pattern of expression as compared to known fingerprint expression profiles of the particular cell type in animals exhibiting cardiovascular disease symptoms. The ability of smooth muscle cells to be taken up by phagocytes is of particular interest.

Cells that are down-regulated in CDKN2B activity can be utilized to identify compounds that exhibit anti-cardiovascular disease activity. In the case of monocytes, such phenotypes may include but are not limited to increases in rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ and GM-CSF. Transmigration rates, for example, may be measured using an in vitro system to quantify the number of monocytes that migrate across the endothelial monolayer and into the collagen layer of the subendothelial space.

In vitro systems may be designed to identify compounds capable of activating efferocytosis. Such compounds may include, but are not limited to, peptides made of D- and/or L-configuration amino acids, phosphopeptides, antibodies, and small organic or inorganic molecules. The principle of the assays used to identify compounds that upregulate CDKN2B or calreticulin involves preparing a reaction mixture of the protein and a test compound under conditions and for a time sufficient to allow the two components to interact, and detecting the resulting change in the desired biological activity. Alternatively, a simple binding assay can be used as an initial screening method. These assays can be conducted in a variety of ways. For example, one method to conduct such an assay would involve anchoring a protein or a test substance onto a solid phase and detecting complexes anchored on the solid phase at the end of the reaction.

In a binding assay, the reaction can be performed on a solid phase or in liquid phase. In a solid phase assay, the nonimmobilized component is added to the coated surface containing the anchored component. After the reaction is complete, unreacted components are removed under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a binding reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

Cell-based systems such as those described above may be used to identify compounds that act to ameliorate cardiovascular disease symptoms. For example, such cell systems may be exposed to a test compound at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype.

In addition, animal-based disease systems, such as those described, above may be used to identify compounds capable of ameliorating disease symptoms. Such animal models may be used as test substrates for the identification of drugs, pharmaceuticals, therapies, and interventions, which may be effective in treating disease. For example, animal models may be exposed to a compound, suspected of exhibiting an ability to ameliorate cardiovascular disease symptoms, at a sufficient concentration and for a time sufficient to elicit such an amelioration of disease symptoms in the exposed animals. The response of the animals to the exposure may be monitored by assessing the reversal of disorders associated with disease, for example, by counting the number of atherosclerotic plaques and/or measuring their size before and after treatment.

With regard to intervention, any treatments that reverse any aspect of cardiovascular disease symptoms should be considered as candidates for human disease therapeutic intervention. Dosages of test agents may be determined by deriving dose-response curves.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

CDKN2B Regulates Efferocytosis and Atherosclerosis

The mechanisms by which genetic variation at the Chromosome 9p21.3 risk locus promote cardiovascular disease remain unclear. Previously, it was reported that loss of one candidate gene at this locus, Cdkn2b, promoted vascular smooth muscle cell (SMC) apoptosis and aneurysm progression. Here we investigate the potential relationship of these findings to atherogenesis, and show that $Cdkn2b^{-/-}$, $ApoE^{-/-}$ mice develop advanced atherosclerotic plaques comprised of large necrotic cores. To explain this observation, we show that loss of CDKN2B impairs expression of calreticulin, a ligand required for activation of engulfment receptors on phagocytic cells. As a result, CDKN2B-deficient apoptotic bodies are rendered resistant to efferocytosis, and are not efficiently cleared by neighboring macrophages. These uncleared SMCs elicit a series of pro-atherogenic paracrine responses, and are associated with increased foam cell formation and inflammatory cytokine elaboration. In total, these data suggest that one mechanism by which loss of CDKN2B promotes atherosclerosis is by increasing the size and complexity of the lipid-laden necrotic core through impaired efferocytosis.

CDKN2B is a well-described cell-cycle inhibitor that is frequently lost during malignant transformation, but had not previously been implicated in vascular disease. It was recently reported that CDKN2B does play a role in vascular SMC physiology, and that Cdkn2b knockout mice develop advanced aneurysms related to accelerated SMC apoptosis and medial thinning (Leeper et al. (2013) *Arterioscler Thromb Vasc Biol* 33:e1-e10). However, the mechanism(s) by which 9p21 promote coronary disease remain unclear and the subject of debate.

Results:

Cdkn2b regulates atherosclerotic lesion size and features of plaque vulnerability in vivo. To study the effect of Cdkn2b on atherosclerosis in vivo, we evaluated a total of 44 male $Cdkn2b^{-/-}$,$ApoE^{-/-}$ and $Cdkn2b^{+/+}$,$ApoE^{-/-}$ mice after 12 weeks of high-fat Western diet. Total atherosclerotic burden was increased in $Cdkn2b^{-/-}$,$ApoE^{-/-}$ animals, as measured by the Oil-Red-O (ORO) positive area within the aortic sinus (34% increase, P=0.001, FIG. 1A). Additionally, these lesions displayed several features of plaque vulnerability, including reduced lesional smooth muscle alpha actin (SMA) content (34.0% reduction, P<0.02, FIG. 1B) and larger necrotic cores (37% increase, P<0.03, FIG. 1O and FIG. 7A), with no change in Mac-3 staining (P=0.26, FIG. 1D). Similar findings were observed in the brachiocephalic artery, where $Cdkn2b^{-/-}$,$ApoE^{-/-}$ lesions displayed decreased collagen content (50.2% reduction, P<0.05, FIG. 1F), reduced SMA content (34.1%, P<0.02, FIG. 1G), and thinning of the fibrous cap overlying the necrotic core of the lesion (54.2% reduction, P<0.04, FIG. 1H). No change in macrophage content was observed between genotypes (P=0.89, FIG. 1I). At this terminal endpoint, very few TUNEL positive cells were present (~0-2/section), and no difference in apoptosis was observed between genotypes (38.5% increase in TUNEL positive cells, P=0.54, FIG. 1E). Conversely, $Cdkn2b^{-/-}$,$ApoE^{-/-}$ mice infused with Angiotensin 11 for 72 hours at an early timepoint (4 weeks Western diet) displayed a 97% increase in apoptotic cells, relative to control (P=0.06, FIG. 7B). The compensatory expression of other 9p21-locus genes is provided in FIG. 7C. No difference in glucose or lipid levels was observed across genotypes (FIG. 7D).

Reduced expression of CDKN2B is associated with reduced expression of the phagocyte receptor ligand, calreticulin, in human coronary artery atherosclerotic plaque, human vascular SMC, and mouse aorta. To explain the larger necrotic cores observed in the $Cdkn2b^{-/-}$,$ApoE^{-/-}$ mice, we next evaluated the expression of several pro- and anti-phagocytic molecules (known as "eat-me" and "don't-eat-me" ligands, respectively) in 51 human coronary artery sections with and without atherosclerotic lesions. We first evaluated the relationship between CDKN2B and 28 genes that have previously been implicated in the clearance of apoptotic debris, a process known as 'efferocytosis'.

Weighted gene co-expression network analysis revealed two modules of efferocytosis gene expression (FIG. 8A). The module which contains CDKN2B had significantly lower expression, as quantified by module eigengene analysis, in samples with atherosclerotic lesions than in those without atherosclerotic lesions (log 2 expression 0.16 vs. 0.27, for samples with and without lesions, respectively, P=0.00000016, FIG. 2A). We next used naïve expression clustering of all 20,226 transcripts annotated on the array into 51 modules using weighted gene co-expression analysis to identify genes that share local co-expression topology with CDKN2B.

Figure 2:
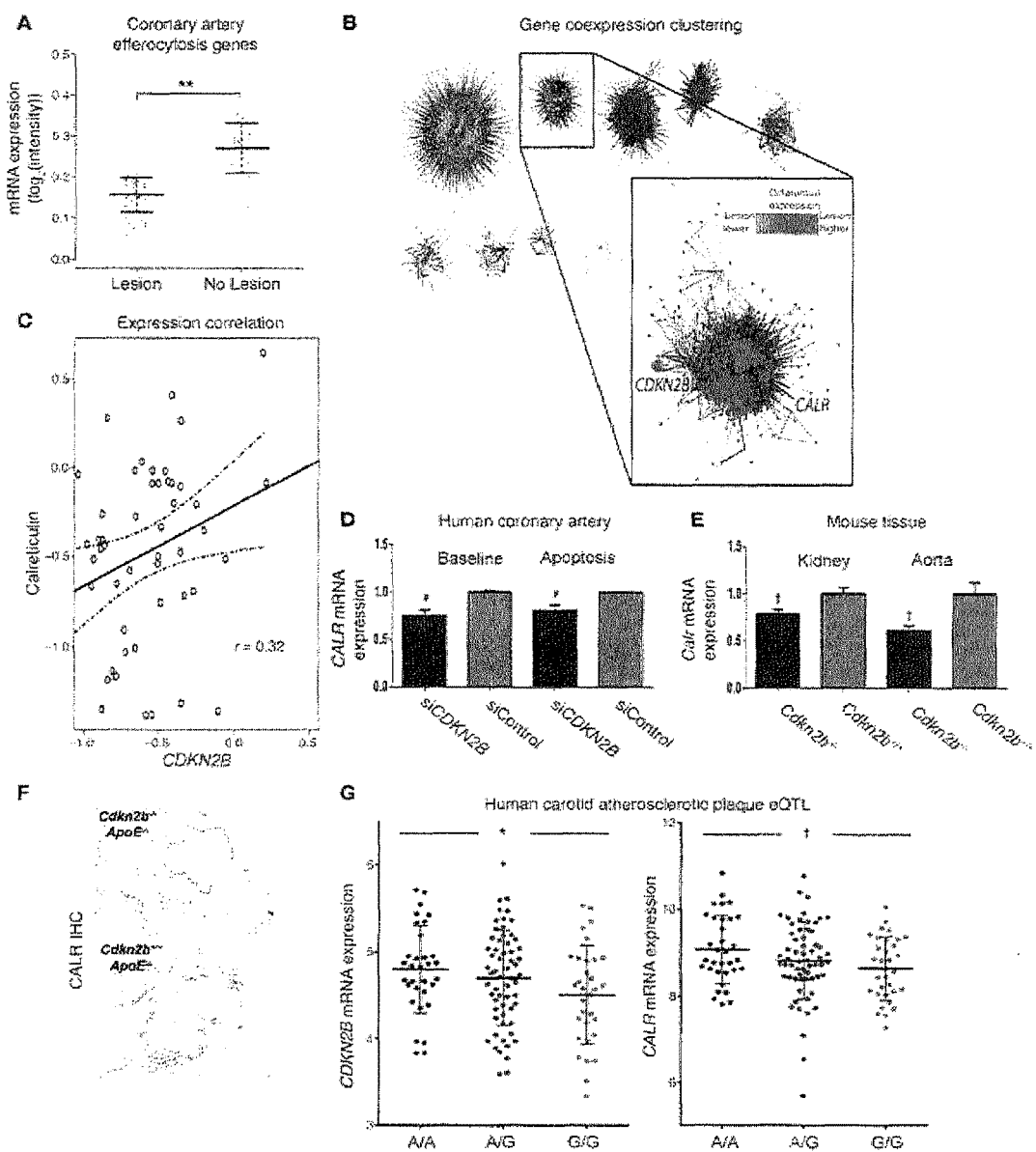
FIG. 2. Loss of CDKN2B is associated with reduced expression of the key phagocyte-receptor ligand, calreticulin. Weighted gene coexpression analysis of 51 human coronary artery segments revealed that CDKN2B co-localizes with CALR in (A) local coexpression topology with efferocytosis genes that are down regulated in coronary artery samples with atherosclerotic lesions compared with samples without atherosclerotic lesions, and (B) global module discovery in weighted gene coexpression analysis of 20,226 transcripts. (C) CDKN2B is directly correlated with CALR expression in coronary artery sections. In all network diagrams the edge width corresponds to the topological overlap between linked nodes. Node color in network graph corresponds to module assignment. Inset depicts module containing CDKN2B and CALR identified via hierarchical clustering of the topological overlap between all transcript pairs. Node color in inset corresponds to differential expression of module members in coronary artery samples with atherosclerotic lesions versus those without atherosclerotic lesions. For simplicity, only edges corresponding to a topological overlap>0.2 are displayed. (D) A similar pattern was observed in vitro, as CDKN2B-deficient HCAMSC expressed lower levels of CALR than control-transfected HCASMC, both at baseline and during apoptosis. (E) Cdkn2b$^{-/-}$,ApoE$^{-/-}$ mice also expressed less Calr than Cdkn2b$^{+/+}$,ApoE$^{-/-}$ mice in both the kidney and aorta. (F) Semiquantitative immunostaining confirmed the reduction of Calr expression in atherosclerotic plaque from Cdkn2b$^{-/-}$, ApoE$^{-/-}$ animals. (G) eQTL analysis of 127 human carotid artery atherosclerotic plaque samples revealed that carriers of a representative 9p21 risk allele ("G" in red, relative to ancestral "A" allele in black) have simultaneous reductions in the expression of both CDKN2B (left panel, *P<0.05) and CALR (right panel, +P<0.03).

Of the candidate efferocytosis genes, only calreticulin (CALR), a key phagocyte receptor ligand, was found in the co-expression module to which CDKN2B was assigned (FIG. 2B, global gene and module summary in Table 1). CALR was positively correlated with CDKN2B expression (rho2=0.32, P=0.02, FIG. 2C), such that patients with impaired vascular CDKN2B also had reduced expression of CALR, in vivo. Similar findings were observed in CDKN2B-deficient (siCDKN2B) human coronary artery SMC (HCASMC) at baseline and during apoptosis, in vitro (P<0.01 each, FIG. 2D and FIGS. 8D-E), and in Cdkn2b$^{-/-}$ aortic and kidney tissue, in vivo (P<0.01 each, FIG. 2E). Semiquantitative immunostaining confirmed the downregulation of CALR in atherosclerotic plaque from Cdkn2b$^{-/-}$, ApoE$^{-/-}$ mice (FIG. 2F).

Calreticulin expression is regulated by a pathway that includes CDKN2B, Retinoblastoma and E2F4 To investigate the molecular link between CDKN2B and CALR, we next examined the CALR promoter for putative transcription factor (TF) binding sites which might be related to the CDKN2B pathway (FIG. 9A). E2F4, an inhibitory transcription factor downstream of TGF-β, CDKN2B and Retinoblastoma (Rb), was identified as a candidate regulatory element by several TF prediction algorithms (FIG. 3A). Electrophoretic mobility shift assays (EMSA) revealed that the top E2F4 binding site within the CALR promoter (−150 bp from TSS, FIG. 9C) bound nuclear proteins from HCASMC, in vitro (FIG. 3B, black arrow). The binding pattern was similar to that observed in a reaction containing a positive control E2F4 binding site (FIG. 9D). Specificity of this binding reaction was confirmed in competition with unlabeled CALR promoter probe included at 100× excess (FIG. 3B, black arrowhead). Subsequent chromatin immunoprecipitation (ChIP) studies confirmed that this sequence specifically bound the E2F4 transcription factor in HCASMC, in vivo, with 3.7 fold enrichment compared to IgG control (4.6 vs. 1.2% of input, P<0.01, FIG. 3C).

Next, luciferase promoter reporter assays were used to show that the activity of the CALR promoter was dependent on both CDKN2B and Rb, where HEK cells overexpressing these genes showed increased CALR promoter activity (2.7-3.4 fold increase, P<0.01, FIG. 3D, bottom), while HEK cells transfected with siCDKN2B displayed reduced CALR promoter activity (37% reduction, P<0.01, FIG. 3D, top). Finally, we showed that CALR expression could be increased in response to TGF-β treatment in a dose-dependent manner, and that this expression was significantly inhibited when either CDKN2B or Rb signaling was impaired with siRNA (FIG. 3D). Taken together, these data suggest that CALR expression is regulated by a cascade that involves the vascular cytokine, TGF-β, the 9p21-related candidate gene, CDKN2B, and the Rb-E2F4 axis.

Reduced expression of CDKN2B renders SMCs resistant to efferocytic clearance by both professional and non-professional phagocytes, without altering the phagocytic capacity of neighboring SMCs. To explore the physiological consequences of a loss of CDKN2B, we next performed a series of efferocytosis assays to investigate the impact of this gene on the 'edibility' of apoptotic bodies (AB) and the efferocytic capacity of phagocytic cells. In these experiments, control or CDKN2B-deficient cells were fluorescently labeled green, rendered apoptotic, then co-cultured with orange-labeled phagocytes prior to flow cytometry analysis. Apoptotic siCDKN2B HCASMCs were cleared less efficiently than apoptotic control transfected (siCont) HCASMCs by both professional and nonprofessional phagocytes (52.4% less efferocytosis by PMA-transformed THP-1 macrophages, P<0.01, FIG. 4A, and 20.0% less efferocytosis by untransfected nonapoptotic neighboring HCASMC, P<0.02, FIG. 4B, respectively). Phagocytosis competition assays confirmed that siCDKN2B AB were less likely to be engulfed than siCont AB in a simultaneous co-culture assay (19.1% fewer cleared cells per HPF, P<0.02, FIG. 4C). All assays were repeated and confirmed with primary Cdkn2b$^{-/-}$ and Cdkn2b$^{+/+}$ aortic smooth muscle cells and thioglycollate-stimulated intraperitoneal macrophages.

Figure 4:
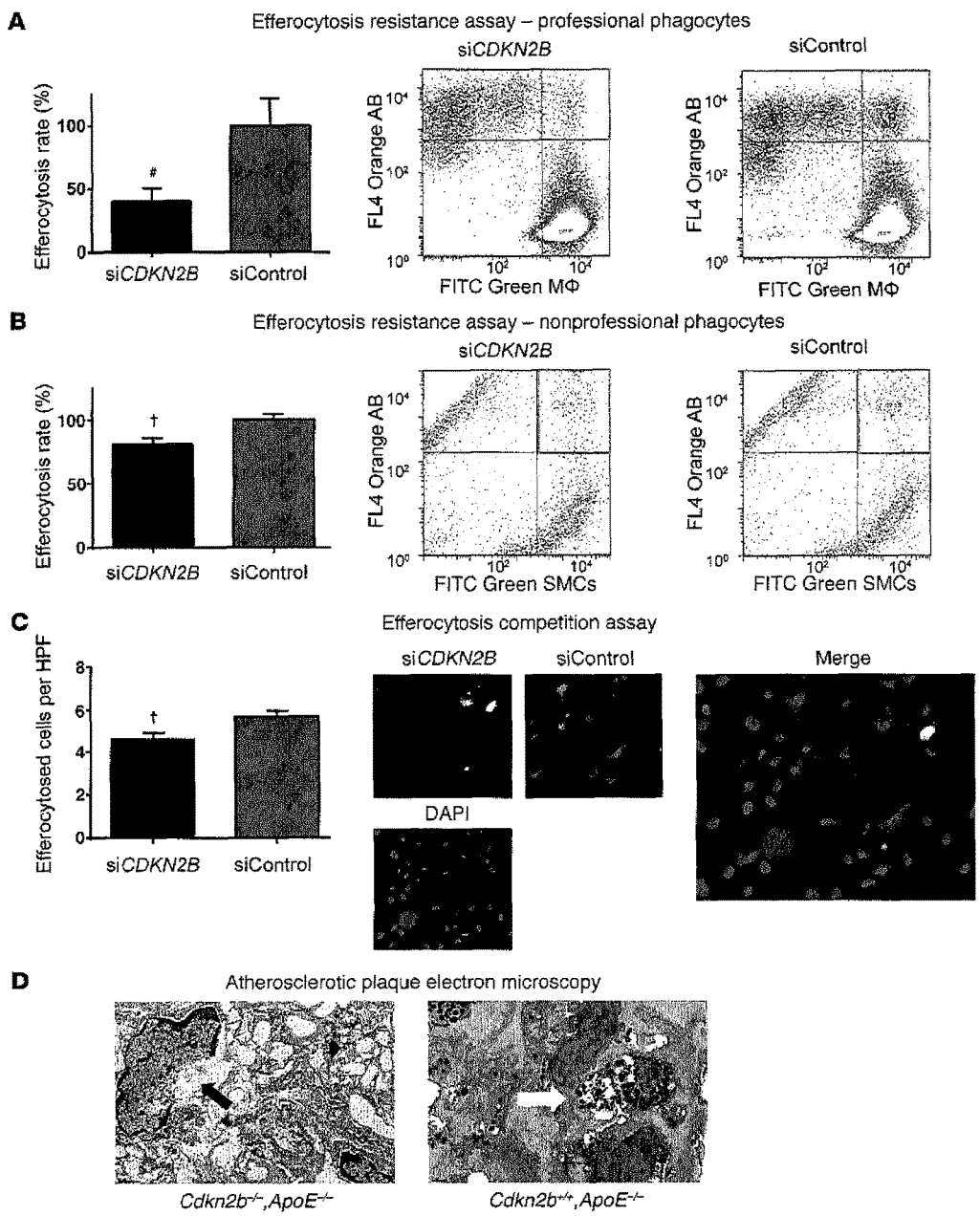
FIG. 4. Loss of CDKN2B renders apoptotic SMCs 'inedible'. (A) Flow cytometry-based phagocytosis assays revealed that apoptotic CDKN2B-deficient smooth muscle cells were significantly less likely to be cleared by primary macrophages than control apoptotic bodies (AB). (B) Apoptotic CDKN2B-deficient HCASMC were also resistant to efferocytic clearance by neighboring SMCs, which are known to function as non-professional phagocytes in conditions such as atherosclerosis. (C) Efferocytosis competition assays revealed that control-transfected AB were more likely to be phagocytosed than CDKN2B-deficient AB when co-cultured with phagocytes in equal numbers. (D) Qualitative electron microscopy images revealed evidence of SMC necrosis in plaques from Cdkn2b$^{-/-}$,ApoE$^{-/-}$ mice, as indicated by cells with condensed chromatin and disrupted plasma membranes (black arrows) and extracellular lysosomes suggestive of cellular rupture (black arrowheads). Conversely, plaques from Cdkn2b$^{+/+}$,ApoE$^{-/-}$ mice harbored little necrotic debris and were populated by phagocytes which had each engulfed numerous AB, suggesting more robust efferocytic clearance (white arrows).

Importantly, knocking down CDKN2B in non-professional phagocytes (e.g. HCASMCs), had no effect on their capacity to phagocytose co-cultured AB (P=0.95, FIGS. 10A-B). Professional phagocytes (e.g. RAW, PMA-transformed THP-1, and primary murine peritoneal macrophages) had undetectable CDKN2B expression in vitro at baseline or after LPS stimulation. Qualitative electron microscopic evaluation revealed that atherosclerotic plaques from Cdkn2b$^{-/-}$, ApoE$^{-/-}$ animals displayed several features of failed efferocytosis, including large numbers of cells which had progressed from apoptotic to necrotic bodies as well as ABs not associated with an adjacent macrophage (FIG. 4D and FIG. 10C). Conversely, plaques from Cdkn2$^{+/+}$, ApoE$^{-/-}$ mice had less extracellular necrotic debris and displayed significant numbers of phagocytes which had ingested multiple AB suggestive of efficient clearance of dying cells.

Macrophages exposed to CDKN2B-deficient SMCs downregulate the ABCA-1-dependent cholesterol efflux pathway, display accelerated rates of foam cell transformation, and secrete pro-atherogenic cytokines. Because the loss of efferocytosis ligand expression on an AB has previously been shown to alter the behavior of the neighboring phagocyte, we next assessed the paracrine effects of CDKN2B-deficient AB on co-cultured macrophages. In particular, we focused on the macrophages' capacity to regulate lipid handling and inflammation, as these are processes known to be related to efferocytosis. RAW macrophages co-cultured with apoptosing siCont SMC increased their expression of the key reverse cholesterol transport molecule, Abca1, compared to baseline (15.9 fold increase, p<0.001, FIG. 5A, grey bar), as previously described. However, those macrophages exposed to apoptosing CDKN2B-deficient SMCs displayed a blunted increase (9.7 fold, P<0.001, black bar). This assay was confirmed with primary Cdkn2b$^{-/-}$ and Cdkn2b$^{+/+}$ aortic smooth muscle cells and RAW macrophages. A similar reduction in Abca1 mRNA level was observed in Cdkn2b$^{-/-}$, ApoE$^{-/-}$ aortic tissue, relative to control aortas (65% reduction, p<0.01, FIG. 5B).

Figure 5:
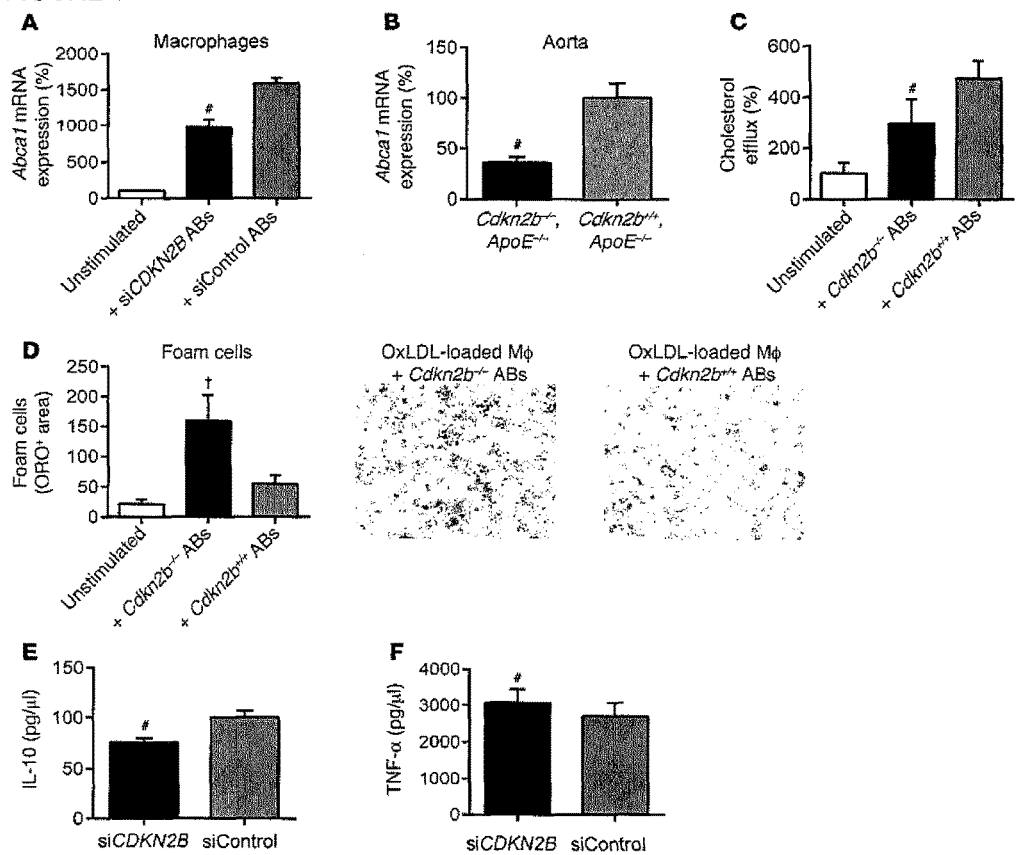
FIG. 5. Macrophage biology is perturbed by interactions with apoptotic CDKN2B-deficient SMC. (A) Macrophages co-cultured with siCont AB (grey bar) upregulated Abca1, a key reverse cholesterol transport gene, relative to baseline (white bar). This homeostatic pathway was significantly blunted when macrophages were co-cultured with siCDKN2B AB (black bar). (B) Aortic expression of Abca1 was also reduced in Cdkn2b$^{-/-}$,ApoE$^{-/-}$ animals relative to Cdkn2b$^{+/+}$,ApoE$^{-/-}$ control mice. (C) Similarly, macrophages co-cultured with Cdkn2b$^{+/+}$ AB (grey bar) displayed the expected increase in tritium labeled cholesterol efflux relative to baseline (white bar), but a blunted response was observed for macrophages co-cultured with Cdkn2b$^{-/-}$ AB (black bar). (D) As a result, foam cell formation was accelerated when ox-LDL loaded macrophages were co-cultured with Cdkn2b$^{-/-}$ AB (black bar) compared to Cdkn2b$^{+/+}$ AB (grey bar). (E-F) Macrophages co-cultured with siCDKN2B AB secrete less anti-inflammatory IL-10 and more pro-inflammatory TNF-α (black bars), relative to macrophages co-cultured with siCont AB (grey bars).

To assess the physiological consequence of this reduction in Abca1, we performed radioactive cholesterol efflux studies, and found that RAW cocultured with siCont AB did significantly increase their efflux of [$^3$H]-labeled cholesterol compared to baseline (4.7 fold increase, P<0.001, FIG. 5C, grey bar), but that this change was blunted when RAW cells were co-cultured with siCDKN2B AB (2.9 fold increase, P=0.02, FIG. 5C, black bar). Consequently, we also observed that cholesterol-loaded macrophages exposed to CDKN2B-deficient SMCs were more likely to assume the foam cell phenotype, as quantified by total Oil-Red-O content compared to macrophages co-cultured with control AB (2.9 fold increase in ORO positive area between conditions, P=0.03, FIG. 5D). Ultimately, the downstream consequence of this failed efferocytosis and accelerated foam cell formation was the assumption of a pro-atherogenic profile, where macrophages co-cultured with CDKN2B-deficient SMC secreted higher levels of TNF-α and lower levels of the anti-inflammatory cytokine, IL-10, relative to macrophages co-cultured with control-transfected SMC (14.2% increase and 24.4% decrease, P<0.01 for each, respectively, FIGS. 5E-F).

Understanding how the 9p21 cardiovascular risk locus potentiates disease has proven challenging. The present study demonstrates how CDKN2B, a gene which may be dysregulated in carriers of the 9p21 risk allele, contributes to this risk. These data show that CDKN2B regulates the clearance of apoptotic debris, and thus alters the composition and size of the developing plaque.

First, we show that loss of Cdkn2b is associated with advanced atherosclerotic lesions comprised of large, lipid-laden necrotic cores. Second, we show that CDKN2B-deficient apoptotic SMCs resist phagocytic clearance, providing an explanation for the observed acceleration in plaque growth. Mechanistically, we show that TGF-β signals through an Rb-dependent cascade to initiate a phagocyte recognition signature, but that loss of CDKN2B impairs the expression of the key phagocyte-receptor ligand, calreticulin. Finally, we show that this contributes to pathological downstream cross-talk with neighboring macrophages, reduces reverse cholesterol transport, and promotes inflammation and foam cell generation. Taken together, these findings provide mechanistic insights into the heritable component of cardiovascular disease, explain how the top GWAS hit promotes risk independently of classical risk factors, and serves as a target for novel translational therapies directed against atherosclerotic disorders.

It has been estimated that as many as one million cells undergo programmed cell death per second each day in the human body. Despite the frequency of this event, apoptotic cells are rarely observed in vivo, even in organs with high basal turnover rates such as the bone marrow or thymus. This observation is attributed to the fact that apoptotic bodies are rapidly and efficiently cleared by both professional (i.e. macrophage) and non-professional (i.e. neighboring cell) phagocytes. Previously considered an obligate homeostatic event, the process of 'efferocytosis' (from the Greek: to carry the dead to the grave) is now appreciated to occur as the result of highly orchestrated paracrine signaling between the AB and its potential phagocyte. During programmed cell death, apoptosing cells secrete chemotactic "find-me" ligands, upregulate cell-surface "eat-me" ligands, and repress inhibitory "don't-eat-me" signals. Remarkably, this process occurs in an "immunologically silent" manner, where the successful execution of the engulfment process triggers an anti-inflammatory cytokine profile from the phagocyte, presumably as a signal that no further immune activation is required. Conversely, apoptotic cells which evade clearance rapidly become secondarily necrotic and induce an inflammatory 'danger response' as they release toxic and antigenic intracellular content which was previously sequestered. Impaired efferocytosis is now recognized as a major driver of autoimmune, inflammatory and malignant disorders, where failed immune surveillance is thought to result from an imbalance in the pro- and anti-phagocytosis signatures on target cells.

Atherosclerosis is a condition in which apoptosis is dramatically accelerated. Complicating this is the fact that efferocytosis may be reduced by nearly ~20-fold as the human atherosclerotic plaque develops. The reason for this defect is not clear, but is likely related in part to competition for phagocyte receptors by oxidized LDL and/or the generation of autoantibodies which mask important cell-surface ligands on the apoptotic body. Moreover, experimental atherosclerosis models can be significantly accelerated by inhibiting the expression of 'eat-me' ligands in mice, and these animals display lesions with advanced necrotic cores replete with apoptotic corpses. Impaired efferocytosis likely has important clinical consequences in atherogenesis, given that delayed clearance of dying SMCs has been linked to vascular inflammation and matrix destabilization, and that residual necrotic debris frequently localizes to regions of the lesion most susceptible to rupture. The fact that loss of Cdkn2b in mice increases the size of the plaque and its lipid core while reducing the thickness and stability of the fibrous cap may partially explain the simultaneous link in humans between 9p21 and both total CAD burden and acute clinical events, such as myocardial infarction. Impaired efferocytosis may also promote atherosclerosis secondarily through the phagocyte.

Emerging evidence has revealed that the phenotype of the apoptosing cell can have a dramatic impact on the behavior of the nearby macrophage and its ultimate capacity to maintain lipid homeostasis. Under physiological conditions, macrophages which have successfully engaged an apoptotic body upregulate transmembrane export pathways downstream of LRP-1 and a variety of nuclear receptors, presumably in preparation for the impending doubling of their intracellular content. A key effector molecule in this pathway is ABCA1, which promotes reverse cholesterol efflux and is important for limiting the local accumulation of cholesterol in the fatty streak. In the current study, macrophages presented with CDKN2B-deficient apoptotic bodies failed to activate this pathway and could not process oxidized lipids efficiently. Mechanistically, this likely occurred because CDKN2B deficient cells express low levels of CALR, which is a well described ligand for the LRP-1 receptor. As a consequence, these otherwise healthy macrophages displayed a blunted increase in ABCA1 expression and were more likely to differentiate into foam cells—a process which is recognized as maladaptive and pro-atherosclerotic. Thus, while the efferocytic capacity of the phagocyte is not altered by its basal CDKN2B expression (FIG. 10B), its ultimate participation in the atherogenesis process is highly dependent on whether it encounters a 'normal' AB, or one that has been rendered 'inedible' due to a lack of CDKN2B (FIG. 6).

These data show that CDKN2B mediates its phagocytic effects through calreticulin. Calreticulin is an evolutionarily conserved 46 kD chaperone protein which regulates a variety of cellular functions including calcium homeostasis, cell adhesion, wound healing, immunity, fibrosis and the response to stress. Additionally, CALR has been implicated as one of the major regulators of efferocytosis, and is a critical engulfment ligand which is absolutely required for phagocytic clearance. During apoptosis, CALR co-localizes to the surface of the AB with exposed phosphatidylserine and activates LRP-1 on the surface of the adjacent macrophage. Interestingly, prior studies have shown that mice deficient in this CALR receptor phenocopy several aspects of the CDKN2B-deficient mouse, including the propensity to develop large aortic aneurysms and advanced lipid-laden atherosclerotic plaques, with no difference in plasma lipoprotein levels (reviewed in Boucher and Herz (2011) Bio-

*chem Pharmacol* 81:1-5). Further, CALR has also been identified as a key regulator of tumor surveillance and the clearance of malignant cells.

Several agents, including HMG-Co-A reductase inhibitors (statins), have been shown to augment phagocytosis, but likely not to the level required for restoration of physiologic cell processing. Such efforts are now underway in the oncology field, with the hopes of triggering the removal of cells which have evaded the reticuloendothelial system. Because the 9p21 locus promotes risk independently of all classical risk factors, a therapy that promotes efferocytosis can provide incremental benefit beyond antihypertensives, antidiabetics and lipid lowering therapies. The currently available data suggest that CDKN2B specifically mediates its effect through the LRP-1-cholesterol efflux pathway, as loss of CDKN2B on the ApoE*3Leiden transgenic background (a strain which increases its systemic lipid levels in response to nuclear receptor activation upstream of Abca1) was not associated with advanced atherosclerosis in a previous study. Given that first line anti-atherosclerotic therapies such as atorvastatin, simvastatin and rosuvastatin may suppress the ABCA1 pathway, methods to reactivate the expression of this critical antiatherogenic gene might be particularly desirable in carriers of the 9p21 risk allele.

Methods:

Murine Atherosclerosis Studies.

Animals used in this study included male $Cdkn2b^{+/+}$, $ApoE^{-/-}$ (n=27, Jackson Laboratory) and $Cdkn2b^{-/-}$, $ApoE^{-/-}$ (n=27) mice on a C57BL/6 background, which were bred by our laboratory as previously described. At 4 weeks of age, the animals were weaned and initiated on a high fat Western diet (21% anhydrous milk fat, 19% casein and 0.15% cholesterol, Dyets no. 101511) for the ensuing weeks. Animals were observed daily, and in the case of premature sudden death, necropsy was performed to determine the cause of death. Lipid analysis was performed in mice after an overnight fast, as previously described. In brief, total plasma cholesterol (CHOD-PAP; Roche Diagnostics), HDL (HDL-C-plus 2nd generation; Roche Diagnostics), and LDL concentrations (GPO-PAP; Roche Diagnostics) were measured using enzymatic kits on an automated analyzer (Roche) according to the manufacturer's instructions. Fasting glucose was measured in venous blood from a tail prick using a Freestyle Glucometer and glucose strips (Abbott). At 16 weeks of age, the mice were euthanized and the aortas were isolated and processed for analysis. A subset of ten mice were implanted with subcutaneous osmotic minipumps (Alzet, Model 2004) after only four weeks of high-fat diet, to deliver 1.4 mg/kg/day of Angiotensin II for 72 hours prior to sacrifice to enhance vascular injury in early atherosclerotic lesions. All studies were approved by the Stanford University Administrative Panel on Laboratory Animal Care and conform to the Guide for the Care and Use of Laboratory Animals published by the US National Institutes of Health.

Aortic and Brachiocephalic Tissue Preparation, Immunohistochemistry and Atherosclerotic Lesion Quantification.

Aortic atherosclerosis lesion area was determined as described previously. Briefly, the arterial tree was perfused with PBS (pH 7.3) and then perfusion fixed with phosphate-buffered paraformaldehyde (3%, pH 7.3). The heart and the full-length of the aorta-to-iliac bifurcation was exposed and dissected carefully from any surrounding tissues. Aortas were then opened along the ventral midline and dissected free of the animal and pinned out flat, intimal side up, onto black wax. Aortic images were captured with a digital camera mounted on a Nikon stereomicroscope and analyzed using Adobe Photoshop CS5 software. The percentage of lesion area was calculated as total lesion area divided by total surface area. The atherosclerotic lesions in aortic valve area and proximal brachiocephalic artery were analyzed as described previously. The samples were perfused with PBS, fixed with paraformaldehyde (4%), embedded in OCT, and sectioned at 7-μM thickness. Three sections at 100-μM intervals were collected from each mouse and stained with Oil Red O (Sigma-Aldrich, 00625), Masson Trichrome (Sigma Aldrich, St. Louis, Mo., USA), Picrosiruis Red (Polysciences, #24901), haematoxylin and eosin (H&E), smooth muscle α-actin (SMA, Abcam, ab5694, 1:300), Mac-3 (BD Sciences BD 550292, 1:75), CD-3 (Abcam, ab5690, 1:150), and Calreticulin (Abcam, ab2907, 1:300). Biotinylated secondary antibodies followed by avidin-biotin-alkaline phosphatase substrate were used as previously described.

In vivo apoptosis was assessed by staining for TUNEL positivity with the Cell Death Detection Kit (Roche), per protocol. Cellular proliferation was measured by staining with PCNA (Abcam, ab2426, 1:500). The cellularity of the vessel was measured by manually counting nuclei of sections stained with DAPI. Negative controls were performed with the omission of the primary antibody. The lesion areas were measured and quantified using Adobe Photoshop. Features of atherosclerotic plaque vulnerability were assessed as previously described. Briefly, the size of the necrotic core was measured by calculating the percentage of the lesion which was acellular on H&E staining. The cap thickness was measured by placing a 12 point compass in the center of the blood vessel and averaging the thickness of the cap at each point as it crossed the lesion. SMC cap coverage was measured by calculating the percentage of the fibrous cap surface which stained positive for SMA-actin. Other standard features were assessed as described. Samples harvested from several tissue beds were also snap frozen in liquid nitrogen for subsequent gene expression analysis, as described below. Electron microscopy was performed in the Cell Sciences Imaging Facility by the Stanford Electron Microscopy Core on a Jeol TEM1230.

Human Atherosclerotic Plaque Harvest and Gene Coexpression Network Analysis.

Details of sample collection, RNA isolation, and microarray hybridization have been previously described. In brief, epicardial coronary arteries were harvested by dissection from explanted hearts of 22 patient donors for orthotopic heart transplant. Arterial segments were identified as containing atherosclerotic lesions (n=38) or not (n=13) by microscopic inspection. RNA was isolated from each sample and hybridized to a custom dual-dye gene expression microarray (Agilent; Palo Alto, Calif.) representing 20,226 transcripts identified via sequencing clones from stimulated vascular cells, literature review for genes important to cardiovascular function, and combination with a commercial clone set (Incyte). Arrays were scanned using Agilent's G2565AA Microarray Scanner System and Agilent feature extraction software was used to generate log 2 ratios and P values for features on the array. Prior to gene coexpression network analysis, probe set identifiers were mapped to the current NCBI refseq gene build (hg19) and median values were taken for probes matching the same transcript ID. The general framework for weighted gene coexpression network analysis is described.

Pair-wise Pearson correlation between gene expression values was calculated for every gene in the dataset for a) samples with atherosclerotic lesions, b) samples without atherosclerotic lesions, c) all samples. A soft thresholding parameter β was chosen to satisfy scale-free topology criterion based on R2 maximization for a linear fit with slope −1 to log(k) vs. log(n(k)), effectively "noising down" weak correlations. The topological overlap between genes was calculated according to the method described by Yip and Horvath, generating a network adjacency based on shared network neighbors for all gene pairs. We next used average linkage hierarchical clustering and the dynamic tree cut algorithm, which iteratively searches for stable clusters, to partition the topological overlap network into modules. Singular value decomposition was used to identify the module "eigengene" (first principle component) representing the maximum variance in modular gene expression, and the intra-modular and global connectivity for each gene was generated by summing edge weights within modules and within the global network, respectively.

For targeted analysis of the topological relationship between CDKN2B and 28 annotated genes involved in efferocytosis (CALR, MFGE8, CX3CL1, ABCA6, ICAM3, GAS6, APOH, PROS1, C1QB, ANXA1, CD47, LRP1, MBL2, SIRPA, NR1H3, PPARG, LRPAP1, TGFB1, BAI1, TIMD4, CD14, MERTK, CD36, ELMO1, DOCK1, AKT1, PANX1, GULP1), average linkage hierarchical clustering was performed on the reduced topological overlap matrix representing all pair-wise links between these set members and CDKN2B. Module assignment and eigengene calculation was performed as described above. Differential expression analysis according to presence or absence of atherosclerotic lesion was performed by Wilcoxon rank sum test between module eigengene expression values. A p value less than 0.05 was considered statistically significant. Network visualization was performed using Cytoscape 2.8.3 (San Diego, Calif.) to the topological overlap matrix.

Cell Culture Methods.

Human coronary artery SMC (HCASMC, Lonza, Walkersville, Md., passage #3-6) were propagated in SmGM-2 growth media (Lonza) containing 5% FBS. Human THP-1 monocytic cells, human embryonic kidney (HEK-293) and RAW 264.7 macrophages (ATCC) were grown in DMEM-growth media containing 10% FBS. Primary vascular smooth muscle cells were harvested from the aortas of $Cdkn2b^{+/+}$ and $Cdkn2b^{-/-}$ mice, as previously described. Primary activated macrophages were harvested from mice 72 hrs after intraperitoneal injection of 2 ml of 4% thioglycollate, as previously described. To induce growth arrest and the expression of differentiation genes, SMC were serum starved in basal media (SmBM) for 72 hours, according to conventional protocols.

To induce differentiation of THP-1 monocytes into adherent macrophages, cells were treated with 100 nM PMA for 72 hours, as previously described. For knockdown experiments, SMC were transfected with 300 nM of anti-CDKN2B (siCDKN2B) or high-GC negative control (siCont) siRNA (Ambion, Silencer Select, catalog #4390825 and 4390843, respectively) using the high-efficiency Amaxa Nucleofector system (Lonza, protocol U-025). Successful transfection (>85% of all cells) was confirmed by visual fluorescent microscopic analysis and fluorescence activated cell sorting (FACS) flow cytometry for the fluorescently-labeled positive control, pmax GFP (Amaxa). Plates were harvested at 80% confluence for RNA and protein analysis or used for subsequent in vitro analysis. Reproducible knockdown of CDKN2B was confirmed in SMC by quantitative rt-PCR which displayed selective silencing of this gene on the order of ~85%. No off target knockdown was observed for any of the other nearby genes, including CDKN2A, ARF or ANRIL. Apoptosis was induced by treating HCASMC with 1 µM staurosporine (Sigma, S5921) in serum free media for 6 hours prior to analysis or harvest and use in co-culture experiments.

mRNA Isolation and Quantitative Reverse-Transcription.

PCR RNA was isolated from cell lysates using the miRNeasy Mini Kit (Qiagen, Valencia, Calif.) according to the manufacturer's protocol. RNA was isolated from the murine organ samples using the Trizol method (Invitrogen). RNA was quantified with the Nanodrop machine (Agilent Technologies, Santa Clara, Calif.) For quantitation of gene transcription, cDNA was generated with M-MuLV reverse transcriptase, and then amplified on the ABI PRISM 7900HT with commercially available TaqMan primers (Applied Biosystems, Foster City, Calif.) and normalized to 18S internal controls, as previously described. A list of the primers and probes used in these studies is provided in below.

Primer Species: Human APOH Hs00979406_m1, C1QC Hs00757779_m1, ANRIL Hs01390879_m1, ARF Hs99999189_m1, CDKN2A Hs00923894_m1, CDKN2B Hs00793225_m1, CD47 Hs00179953_m1, CALR Hs00189032_m1, GAS6 Hs01090305_m1, ICAM3 Hs00233674_m1, MFGE8 Hs00170712_m1, MTAP Hs00559618 ml.

Species: Mouse Calreticulin Mm00482936_m1, Cdkn2a Mm00494449_m1, Arf Mm01257348_m1, Cdkn2b Mm00483241_m1, Abca1 Mm00442646_m1.

In Vitro Assays and Promoter Analysis, in Silico Bioinformatics.

Transcription factor binding site (TFBS) prediction was determined using the following online bioinformatics tools: TRANSFAC (BIOBASE), TFSearch, PROMO, and MatInspector.

Radioactive Electrophoretic Gel Mobility Shift Assays.

Double stranded oligonucleotides for the top predicted E2F4 binding sites (−150 to −134) within the CALR promoter were generated by annealing the following single stranded oligos: F:5' TGGCAGGGGCGGGC-CCAAGGGCTG 3' and R:5' CAGCCCTTGGGCCCGC-CCCTGCCA 3'.-ATP (Perkin Elmer) using T4 polynucleotide kinase (NEB) for 30 minutes at room temperature and then purified through Sephadex G-50 Quick Spin columns (Roche). After measuring radioactivity, reactions were assembled with 1×EMSA binding buffer, 1 µg poly-dIdC, 10 µg nuclear extract harvested from HCASMC, 100× unlabeled probe (for competitions), -ATP labeled probe, and incubated at room temperature for 30 min prior to protein separation on a 4% TBE gel. Gels were dried on Whatman paper using a heated vacuum drier and proteins were detected on radiographic film.

Chromatin Immunoprecipitation Assays

Chromatin immunoprecipitation (ChIP) was performed according to the Millipore EZ-ChIP protocol with slight modifications. HCASMC were cultured in normal growth media until approximately 75% confluent, and then cultured in the absence of serum and supplements for 24 hours. Cells were fixed in 1% formaldehyde for 10 minutes to cross-link chromatin, followed by quenching with glycine for 5 minutes at room temperature. 2×10^7 cells per condition were collected, and nuclear lysates were prepared as described previously (70). Cross-linked chromatin nuclear extracts were sheared into approximately 500 bp fragments using a Bioruptor (Diagenode) for 3 cycles of 3 minutes (30 s ON, 30 s OFF). Sheared chromatin was clarified via centrifugation at 4 C for 15 minutes. 1×10^6 nuclei per condition was precleared with 20 µg anti-rabbit IgG pre-immune serum (Sigma) and 40 µl Protein G Dynabeads (Invitrogen) for 1 hour on a rotating platform, followed by incubation with 2 μg Rabbit IgG or anti-E2F4 antibody (C-20 SC866 Santa Cruz) overnight.

Immunoprecipitated chromatin samples were then incubated with 60p1 Protein G Dynabeads for 2 hours at 4 C on a rotating platform to capture the protein-DNA complexes. Complexes were washed in Low salt, High salt, LiCl, and TE buffers and then eluted with a buffer containing 100 nM NaHCO3 and 1% SDS. Protein-DNA crosslinks were reversed and samples were treated with RNase A and Proteinase K and free DNA was purified using Qiagen PCR purification kits. Total enrichment was measured using primers designed based on the sequence of the top E2F4 binding site within the Calreticulin promoter (F (−199 to −181):5' AGGTCCAATGGAAAAAGAC 3' and R (+84 to +65):5' CAGAAACTGCTCCTTGAAGT 3'), or a known E2F4 regulatory region (FGFr1 as a positive control (Devel Dynamics 2005 119), or a Negative Control region using the following primers (F:5' CCGGAAGCACTTCTCCTAGA 3' and R:5' AAGAGAGAGCGGAAGTGACG 3').

Semiquantitative PCR was used to verify ChIP products via gel electrophoresis. Quantitative real-time PCR (ViiA 7, Life Technologies) was performed using SYBR Green (Applied Biosystems) assays and fold enrichment was calculated by measuring the delta Ct–delta Ct IgG. Melting curve analysis was also performed for each ChIP primer. Data are representative of at least four independent HCASMC samples with qPCR assays performed in triplicate. Data is presented as the percentage of Input DNA and as fold enrichment of chromatin precipitated with the E2F4 Ab relative to the control IgG.

Luciferase Promoter Reporter Assays.

Calreticulin LightSwitch Promoter Reporter GoClones (RenSP, S721464), Empty vectors (S790005) and Cypridina TK Control constructs (pTK-Cluc, SN0322S) were obtained from SwitchGear Genomics (Menlo Park, Calif.) and transfected into HEK cells using Lipofectamine 2000 (Invitrogen). For knockdown assays, 5 pmol of anti-CDKN2B or control siRNA were co-transfected. For overexpression, CDKN2B (sc319536) and Rb expression plasmid (sc119971) and empty vector (pCMV6) were obtained from Origene and 100 ng of plasmid were co-transfected. Dual luciferase activity was measured with the LightSwitch Dual Assay System after 48 hours using a SpectraMax L luminometer (Molecular Devices), according to the manufacturer's instructions. In some experiments, media was changed to serum-free media after 24 hours of transfection. Studies were performed at baseline, and after the cells had been exposed to escalating doses of recombinant human TGFβ-1 (from Sigma, 0.5-10 ng/mL) for the final 16 hours prior to analysis. Relative luciferase activity (*Renilla/Cypridina luciferase* ratio) is expressed as the percentage change relative to the basal values obtained from control-transfected cells not exposed to TGF-β treatment.

Efferocytosis Resistance and Capacity Assays.

Primary aortic smooth muscle cells generated from Cdkn2b$^{-/-}$ and Cdkn2b$^{+/+}$ mice were labeled with 20 μM orange CMTMR CellTracker fluorescent probes (Life Technologies, C2927) for one hour, then cultured overnight in serum free media. Simultaneously, primary intraperitoneal Cdkn2b$^{+/+}$ macrophages were labeled with 20 μM of green CMFDA CellTracker probe (Life Technologies, C7025) for one hour, then cultured overnight in standard media with serum supplementation. In the morning, the SMCs were induced to undergo apoptosis for 4 hours, then were harvested and manually counted. $1\times10^5$ apoptotic cells were then added to the cultured macrophages and were allowed to co-culture for an additional 1.5 hrs. At that point, all adherent cells were trypsinized and FACS sorted (BD FACSCaliber, 530 nm [FL1] and >575 nm [FL4]), as in previously published protocols. Cells which were dual-positive for green (phagocyte) and orange (SMC) were assumed to represent phagocytosed cells.

The efferocytosis rate was then defined as the percentage of dual positive cells (phagocytosed AB) to orange-positive/ green-negative cells (un-eaten AB). Comparison was made between the rates of clearance for Cdkn2b$^{-/-}$ and Cdkn2b$^{+/+}$ AB. This experiment was performed as above with the following permutations: primary murine aortic SMC vs. primary murine intraperitoneal thioglycollate stimulated macrophages; primary murine aortic SMC vs. murine unstimulated RAW macrophages; transfected HCASMC vs. human PMA-stimulated THP-1 cells.

Finally, the effect of CDKN2B on the 'efferocytic capacity' (vs 'efferocytic resistance') was assessed by performing these experiments with CDKN2B deficient and control transfected phagocytes exposed to untransfected AB. In these experiments, the phagocytic capacity was defined as the percentage of dual positive cells (phagocytes which had eaten an AB) to orange-negative/green-positive cells (phagocytes that had not eaten an AB). All assays were repeated on three occasions with at least three replicates per experiment. Analysis was performed with FloJo 7.6.3.

Efferocytosis Competition Assays.

Confirmation of the preceding studies was performed by plating equal numbers of green CellTracker labeled apoptotic siCDKN2B HCASMC and orange CellTracker labeled apoptotic siCont HCASMC onto unlabeled untransfected non-apoptotic HCASMC in 12-well cell culture plates. All three cell types were co-cultured for an additional 2 hours, and then the non-adherent, non-phagocytosed cells were washed off. The remaining cells were fixed and stained with DAPI and analyzed under an inverted fluorescent microscope. 8 random hpf/well were manually counted by a blinded investigator for efferocytosed cells and the ratio of phagocytosed CDKN2B-deficient AB to control-transfected AB was recorded.

Phagocyte-Apoptotic Body Co-Culture Assays Cholesterol Efflux Culture Assays

Cholesterol efflux assays were performed as described previously, with modification. RAW macrophages were plated on 12-well plates in DMEM containing 10% FBS and labeled with [3H] cholesterol (0.5 μCi/well) for 48 hours. After washing with PBS, the cells were co-cultured with apoptotic Cdkn2b$^{-/-}$ and Cdkn2b$^{+/+}$ aortic smooth muscle cells for 1.5 hours, then incubated in serum free DMEM overnight. The cells were washed and incubated in 350 μl of serum free media containing 10 μg/ml Apolipoprotein A-1 (Sigma) as an acceptor for 4 hours. The media was collected and centrifuged, and the amount of radioactivity was determined by scintillation counter. Cholesterol efflux was expressed as the percentage of counts in the media versus total [3H] cholesterol counts (media plus cell). Baseline efflux (without apoA-1) was subtracted.

Foam Cell Formation Assays.

RAW macrophages were seeded on 96-well plates and cultured overnight. In some experiments, macrophages were treated with 100 ng/ml of Lipopolysaccharide from *Escherichia coli* O111:B4 (LPS, Sigma). Macrophages were co-cultured with apoptotic Cdkn2b$^{-/-}$ and Cdkn2b$^{+/+}$ aortic smooth muscle cells and 100 μg/ml oxidized LDL (Biomedical Technologies Inc.) for 24 hrs. The cells were fixed in 4% paraformaldehyde for 20 min, washed with PBS, and stained with 0.5% oil red O for 5 min. After rinsing in 60% isopropanol and washing, 8 random images/well were taken with an inverted microscope at 20× magnification. Oil red O positive area was analyzed with Adobe Photoshop CS5 software.

Macrophage-specific cytokine expression assays LPS-stimulated (1 µg/mL) RAW macrophages were co-cultured with either siCDKN2B or siCont apoptotic HCASMC in serum free media. Unattached HCASMC was removed by washing with PBS after 1.5 hours, then the cells were cultured in serum free DMEM. After 24 hours of incubation, the supernatant was collected and the level of secreted IL-10 and TNF-α was assessed with ELISAs (R&D Systems) developed specifically for cytokines of murine origin.

Statistical Analysis

Data are presented as mean±SEM. Data were subjected to the Kolmogorov-Smirnov test to determine distribution. Groups were compared using the Mann-Whitney U test for non-parametric data or the Students t-test for parametric data. When comparing multiple groups, data were analyzed by analysis of variance with Bonferroni'spost test. For multiple testing of parametric data, a value of P<0.05 was considered statistically significant. Experiments were replicated at least in quadruplicate and all analyses were performed in a blinded fashion by two separate investigators, unless otherwise specified. Statistical analysis was performed with GraphPad Prism 5.

Example 2

To understand how these Cdkn2b-dependent perturbations in SMC biology might extend to atherosclerotic disease, Cdkn2b/ApoE deficient mice were generated. These atheroprone Cdkn2b$^{-/-}$/ApoE$^{-/-}$ mice were fed animals 12 weeks of high-fat Western diet. As predicted by the GWAS data, it was observed that Cdkn2b$^{-/-}$/ApoE$^{-/-}$ animals developed significantly larger atherosclerotic plaques than ApoE$^{-/-}$ control animals (37% increase, P<0.01). Morphometric analysis revealed that the difference in plaque burden was largely driven by an increase in the size of the lipid-laden necrotic core.

As shown in Example 1, loss of Cdkn2b impairs the expression of SMC calreticulin (Calr), a key "eat-me" ligand required for activation of engulfment receptors; reduces the "efferocytosis" (phagocytic clearance) of apoptotic vascular SMCs; and culminates in accelerated atherogenesis secondary to a striking increase in the growth of the necrotic core. Furthermore, co-culture assays revealed that uncleared Cdkn2b$^{-/-}$ SMCs induce neighboring macrophages to assume a 'foam cell-like' phenotype, with an associated reduction in lipid efflux pathways downstream of the Calr receptor, Lrp-1. Reintroduction of exogenous Calr normalizes the clearance of Cdkn2b-deficient SMCs in vitro, highlighting the therapeutic potential of this pathway.

Implicating Cdkn2b in "efferocytosis"— the phagocytic clearance of apoptotic debris: an increase in the rate at which apoptotic debris was produced in this chronic disease model could not be observed (P=NS for TUNEL and Caspase assays at both Week 4 and Week 12). It was reasoned that loss of Cdkn2b might regulate the rate at which apoptotic debris is cleared in the developing atherosclerotic plaque. This process, known as "efferocytosis" (from the Greek meaning to carry the dead to the grave), was assessed with established in vitro flow cytometry-based co-culture phagocytosis assays.

We found that Cdkn2b-deficient SMCs were in fact 'inedible' relative to Cdkn2b WT SMCs, and resisted clearance by both professional phagocytes (i.e. macrophages) and non-professional phagocytes (i.e. neighboring SMCs) (52% reduction in efferocytosis, P<0.03). Consequently, these cells were more likely to become secondarily necrotic, explaining the observed increase in the growth of the necrotic core in Cdkn2b$^{-/-}$ mice. Electron microscopy confirmed that the 'phagocytic index' of macrophages (quantified by the average number of ingested apoptotic bodies (A.B.) per phagocyte) was impaired directly within the atherosclerotic lesions of Cdkn2b$^{-/-}$ mice, in vivo. Loss of Cdkn2b potently impairs SMC efferocytosis, causing accumulation of apoptotic debris in the developing plaque.

Mapping the mechanism linking CDKN2B to the key "eat-me" ligand, calreticulin (CALR): To explain the mechanism by which Cdkn2b-deficient SMCs resist phagocytic clearance, we evaluated the expression of pro- and anti-phagocytic molecules (known as "eat-me" and "don't-eat-me" ligands, respectively) in 51 human coronary atherosclerotic plaques. Using unbiased genome-wide network analyses, we generated co-expression modules that related CDKN2B levels to the expression of all genes previously implicated in efferocytosis. Using this approach, we found that CDKN2B was directly associated with only one engulfment molecule: the phagocyte receptor ligand, calreticulin (CALR). Using data from two separate validation cohorts (n=128 additional subjects), we have confirmed that CALR and CDKN2B are positively correlated, such that carriers of the 9p21 risk allele have reduced expression of both CDKN2B and CALR in coronary and carotid plaque. In keeping with these human data, Cdkn2b$^{-/-}$/ApoE$^{-/-}$ mice had a 42% reduction in lesional Calr expression, relative to control animals (P<0.05). CALR is a pleiotropic molecule which has been implicated in the phagocytic clearance of malignant and apoptotic cells, but had not previously been associated with atherosclerosis. These studies definitively link CDKN2B to CALR expression in human and murine vascular tissue in vivo, and provide an explanation for how CDKN2B mediates efferocytosis in atherosclerosis.

In carriers of the 9p21 risk allele, CDKN2B is reduced, and this correlates with a reduction in CALR expression. CALR is a conserved and pleiotropic molecule responsible for processes as divergent as ER chaperoning, extracellular fibrosis, and Ca$^{++}$ homeostasis. CALR interacts with a variety of receptors, and is known to stimulate efferocytosis by activating the low density lipoprotein receptor-related protein 1 (LRP-1). LRP-1 is an equally complex molecule, responsible for over 40 known homeostatic processes, beyond endocytosis. Of these processes, Lrp-1 has specifically been implicated in lipid homeostasis and foam cell accumulation, in addition to its role in phagocytic clearance. Impaired activation of Lrp-1, secondary to a Cdkn2b-mediated deficiency of Calr, may have pro-atherosclerotic sequelae beyond the simple accumulation of apoptotic debris.

Cdkn2b and the link to Lrp-1/Abca1-dependent lipid homeostasis in macrophages: Lrp-1 stimulates expression of the critical reverse cholesterol transporter, Abca1. This molecule is responsible for the efflux of intracellular cholesterol to apoA-1, and is mutated in patients with Tangier Disease, who are predisposed to premature foam cell formation. During efferocytosis, Abca1 is highly upregulated, presumably to 'prepare' the phagocyte for the impending doubling of its intracellular lipid content. Abca1 also has important pro-survival and anti-inflammatory effects in the macrophage, which may enable them to continue to participate in the clearance of apoptotic debris in the developing atherosclerotic lesion. Because Cdkn2b-deficient animals express low levels of Calr, this may lead to reduced activation of Lrp-1 and therefore impair Abca1-dependent cholesterol metabolism in neighboring macrophages.

We have found that macrophages appropriately increase their Abca1 expression compared to baseline when co-cultured with apoptotic control SMCs. However, the increase is blunted when those macrophages are exposed to apoptotic CDKN2B-deficient SMCs. In turn, this promotes an associated reduction in cholesterol efflux, an acceleration in foam cell formation, and an increase in inflammatory cytokine elaboration by macrophages co-cultured with Cdkn2b-deficient A.B.s relative to macrophages co-cultured with wild type A.B.s. In vivo, Cdkn2b/ApoE KO mice also display reduced aortic Abca1 expression relative to control aortas. Taken together, the presence of Cdkn2b-deficient SMCs that have evaded phagocytosis is sufficient to induce a number of maladaptive and pro-atherosclerotic processes in adjacent macrophages, which culminate in reduced Abca1 augmentation and increased lipid retention.

Restoration of efferocytosis is an important approach for carriers of the 9p21 risk allele, as they are known to have reduced CDKN2B and are predisposed to impaired CALR-dependent efferocytosis. The application of recombinant Calr peptide to Cdkn2b$^{-/-}$ A.B.s in vitro was sufficient to fully normalize efferocytosis relative to control-transfected cells (FIG. 11), confirming both the reversibility of this defect and its therapeutic potential.

Calr-dependent efferocytosis can be stimulated by inhibiting CD47, for example using novel high-affinity fusion peptides (which serve as a CD47 'sink'). Similarly, antibodies to CD47 and soluble high affinity SIRPα can be used to normalize Calr signaling; restore Cdkn2b-dependent efferocytosis; and reverse the growth of the atherosclerotic plaque.

A humanized anti-CD47 mAb ("Hu5F9-G4") (as described in patent application US 2013-0142786 A1, herein specifically incorporated by reference), was engineered by CDR grafting of mouse sequences into a human IgG4 framework, chosen to minimize recruitment of Fc-dependent effector functions. Hu5F9-G4 displays highly selective and highly efficient binding to CD47, and enables macrophages to phagocytose a wide variety of tumor cells, as well as CDKN2B-deficient SMCs (FIG. 12). This agent is effective in mice, and can be translated into human studies. A cGMP cell line has been produced for the production of recombinant Hu5F9-G4, and will treat Cdkn2b/ApoE deficient mice (to model 9p21-related CV disease) and ApoE$^{-/-}$ mice (to model 'garden variety' CV disease) with either Hu5F9-G4 or IgG control via weekly IP injection (n=15 per group). Animals are sacrificed at 12 or 24 weeks, to study the effect of restored efferocytosis on early and late atherosclerotic plaque development, respectively.

In addition to these prevention studies, animals are treated with 12 weeks of Hu5F9-G4 or IgG antibodies after they have already had 12 weeks of high fat diet, to assess the effect of this treatment on plaque regression and/or stabilization. Relative differences in efferocytosis are quantitated across groups in vivo, with co-localization studies of A.B.'s and macrophages within the plaque (to generate a 'phagocytosis index"). Flow cytometric analysis is performed for circulating apoptotic microparticles in serum, which is another described method to measure the systemic impairment in efferocytosis.

Example 3

Mice.

Male apoE$^{-/-}$ mice (backcrossed onto a C57BL/6 background) were bred by our laboratory as previously described and housed in a specific, pathogen-free environment. Standard sterilized laboratory diet and water were available ad libitum. At Day 0 the animals were initiated on a high fat Western diet (21% anhydrous milk fat, 19% casein and 0.15% cholesterol, Dyets no. 101511) for the ensuing weeks.

AngII Infusion.

Mice (8 to 10 weeks old) were implanted with minipumps that delivered AngII subcutaneously at a dose of 1000 ng/kg$^{-1}$/min$^{-1}$, as described previously (see Daugherty et al. (1999) Ann N Y Acad Sci. 892: 108-118.

Antibodies.

Rat IgG2a monoclonal antibody miap301 (see Jiang et al. (1999) J Biol Chem. 274(2):559-62) reacts with mouse CD47. Normal rat IgG was used as a control. The antibody was injected into the animals at 200 μg/day i.p. with the schedule shown in FIG. 13.

Tissue.

Anesthetized mice were cut open ventrally. Left cardiac ventricles were perfused with phosphate-buffered saline (20 mL) under physiologic pressure with an exit through the severed right atria. Suprarenal regions of abdominal aorta were identified between the last pair of intercostal arteries and the right renal branch. The mesenteric and renal branches and the aorta distal to the right renal branch were ligated with silk sutures, and the suprarenal aorta was harvested. This portion of aorta, measuring ≈5 mm in length, was infused with ≈0.3 mL of OCT compound with a 21-gauge needle to attain full distension. Thoracic aortas between the left subclavian artery and the last pair of intercostal arteries were also harvested. The orientation of aortas was noted, and tissues were frozen immediately.

Pathology and Immunocytochemistry.

Aortas were obtained at selected intervals after the initiation of AngII infusions and antibody treatment, and were sectioned longitudinally or by cross sections (7 μm thick). For characterization of cross sections, aortic sections were collected serially from the proximal to the distal aorta. Histology was determined in sections that were taken at intervals of 200 μm. For longitudinal examination of tissues, 7-μm sections were also placed at 200-μm intervals on slides. Standard histologic staining was performed.

Immunocytochemical staining was performed to identify macrophages (MAC3) and smooth muscle (anti-smooth muscle actin (α-SMA)). At least 2 slides, containing ≈15 tissue sections, from each animal were examined for each cell type. A peroxidase-based ABC system and the red chromogen AEC were used to detect the antigen-antibody reaction. Controls included isotype-matched antibodies and nonimmune sera.

Results

At day 30 the mortality for the control IgG group was 25%, 3 out of 12. All had an aortic dissection. The anti-CD47 treated group had a mortality rate of 16.6% (2 out of 12), and one animal had an aortic dissection.

The atherosclerotic plaque area was measured as a percent of en face thoracic aorta, results shown in FIG. 14. The animals treated with anti-CD47 antibody had reduced plaque relative to the control animals. Atherosclerosis in the aortic sinus was also calculated based on Oil Red O staining, results shown in FIG. 15.

The results of immunohistochemistry with Mac3 and an anti-SMA antibody are shown in FIG. 16. A blood cell differential for the animals is provided in FIG. 17. The ratio of the weight of selected tissues vs. total body weight is shown in FIG. 18.

What is claimed is:

1. A method of reducing atherosclerotic plaque in a human subject, the method comprising:
   genotyping the subject for the presence of at least one 9p21 risk allele, where an individual determined to have a 9p21 risk allele for atherosclerosis is treated, by
   administering to the subject an effective dose of an anti-CD47 polypeptide that reduces the binding of CD47 on an apoptotic cell to Signal regulatory protein alpha (SIRPα) on a phagocytic cell that increases the efferocytosis of cellular components of atherosclerotic plaque, thereby inhibiting atherosclerotic plaque.

2. The method of claim 1, wherein the 9p21 risk allele is genotyped by determination of the presence of an single nucleotide polymorphism (SNP) variant at 9p21 associated with risk.

3. The method of claim 1, wherein the anti-CD47 polypeptide is an antibody that specifically binds CD47.

4. The method of claim 3, wherein the antibody is humanized 5F9-hIgG4.

5. The method of claim 3, wherein the antibody does not activate CD47 upon binding.

6. The method of claim 1, wherein the anti-CD47 agent is a soluble SIRPα reagent.

7. The method of claim 6, wherein the agent is a high affinity soluble SIRPα reagent.

8. The method of claim 1, wherein the anti-CD47 agent specifically binds SIRPα.

9. The method of claim 8, wherein the anti-CD47 agent is an antibody.

* * * * *

SEQUENCE LISTING

<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 1
aggtccaatg gaaaaagac                                                  19

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
cagaaactgc tccttgaagt                                                 20

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 3
ctgttttcag tgccaact                                                   18

<210> SEQ ID NO 4
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 4
catggggccc cgtcggccgc tg                                              22

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
ccggaagcac ttctcctaga                                                 20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
aagagagagc ggaagtgacg                                                 20

<210> SEQ ID NO 7
<211> LENGTH: 24
<212> TYPE: DNA
<213> ORGANISM: Artificial Sequence
<220> FEATURE:

<223> OTHER INFORMATION: synthetic oligonucleotide

<400> SEQUENCE: 7
tggcaggggc gggcccaagg gctg                                          24

<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 8
cagcccttgg gcccgcccct gcca                                          24

<210> SEQ ID NO 9
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 9
caatgacaaa gtggcagggt attgcccaag gctgggtca gg                       42

<210> SEQ ID NO 10
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 10
cctgacccag cccttgggca ataccctgcc actttgtcat tg                      42

<210> SEQ ID NO 11
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 11
atttaagttt cgcgcccttt ctcaa                                         25

<210> SEQ ID NO 12
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 12
ttgagaaagg gcgcgaaact taaat                                         25

<210> SEQ ID NO 13
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 13

Lys Leu Gly Phe Phe Lys Arg
1               5